US012077338B2

United States Patent
Spohn et al.

(10) Patent No.: US 12,077,338 B2
(45) Date of Patent: Sep. 3, 2024

(54) FLUID-CONTAINER AND METHOD FOR CONTROLLING CRYSTALLINITY IN BLOW-MOLDED CONTAINER

(71) Applicant: BAYER HEALTHCARE LLC, Whippany, NJ (US)

(72) Inventors: Michael Spohn, Fenelton, PA (US); Kevin Cowan, Allison Park, PA (US); David Berry, Kittanning, PA (US)

(73) Assignee: BAYER HEALTHCARE LLC, Whippany, NJ (US)

( * ) Notice: Subject to any disclaimer, the term of this patent is extended or adjusted under 35 U.S.C. 154(b) by 185 days.

(21) Appl. No.: 17/625,814

(22) PCT Filed: Jul. 14, 2020

(86) PCT No.: PCT/US2020/041968
§ 371 (c)(1),
(2) Date: Jan. 10, 2022

(87) PCT Pub. No.: WO2021/011558
PCT Pub. Date: Jan. 21, 2021

(65) Prior Publication Data
US 2022/0234779 A1 Jul. 28, 2022

Related U.S. Application Data

(60) Provisional application No. 62/874,236, filed on Jul. 15, 2019.

(51) Int. Cl.
*B65D 1/02* (2006.01)
*B29C 49/06* (2006.01)
(Continued)

(52) U.S. Cl.
CPC ............ *B65D 1/0207* (2013.01); *B29C 49/06* (2013.01); *B29C 49/4273* (2013.01);
(Continued)

(58) Field of Classification Search
CPC ...... B65D 1/0215; B65D 1/0207; B65D 1/40; B29C 35/08; B29C 35/0805; B29C 59/16;
(Continued)

(56) References Cited

U.S. PATENT DOCUMENTS

| 1,020,166 A | 3/1912 | Tibbott |
| 5,254,101 A | 10/1993 | Trombley, III |

(Continued)

FOREIGN PATENT DOCUMENTS

| CA | 2841083 A1 * | 2/2013 | ............. B29B 11/06 |
| EP | 2130782 A1 * | 12/2009 | ......... B29C 49/0005 |

(Continued)

OTHER PUBLICATIONS

"Abstract from WPI Database", Aug. 2, 2012.
"International Preliminary Report on Patentability from PCT Application No. PCT/US2020/041968", Jan. 27, 2022.

*Primary Examiner* — Robert J Hicks
(74) *Attorney, Agent, or Firm* — Joseph L. Kent; James R. Stevenson; David Schramm

(57) ABSTRACT

A fluid container having a proximal end having an end wall, a distal end having an open-ended neck, and a sidewall extending between the proximal end and the distal end along a longitudinal axis is described. A localized crystallinity of a polymeric material of the fluid container of at least a first region of the fluid container is greater than a crystallinity of a polymeric material of the fluid container of at least a second region. Examples of fluid containers include medical fluid containers, such as medical bottles and syringes, including rolling diaphragm-type syringes, and commercial beverage containers Articles of manufacturer formed form a polymeric material and having regions with increased localized polymeric crystallinity are also described.

21 Claims, 12 Drawing Sheets

(51) Int. Cl.
  *B29C 49/42* (2006.01)
  *B29C 49/64* (2006.01)
  *B29C 49/66* (2006.01)
  *B29C 71/00* (2006.01)
  *B29C 71/04* (2006.01)
  *B29K 67/00* (2006.01)
  *B29L 31/00* (2006.01)

(52) U.S. Cl.
  CPC ...... *B29C 49/6605* (2022.05); *B29C 71/0063* (2013.01); *B29C 71/04* (2013.01); *B29K 2067/003* (2013.01); *B29K 2995/0043* (2013.01); *B29L 2031/7158* (2013.01); *B29L 2031/7544* (2013.01); *B65D 2203/06* (2013.01)

(58) Field of Classification Search
  CPC . B29C 49/6605; B29C 49/06; B29C 49/4273; B29C 71/0063; B29C 71/04; B29K 2067/003; B29K 2995/0043; B29L 2031/7158; B29L 2031/7544
  USPC .................. 215/12.1, 12.2; 220/62.22, 62.15; 264/454, 458
  See application file for complete search history.

(56) References Cited

U.S. PATENT DOCUMENTS

| | | | |
|---|---|---|---|
| 5,585,065 A | * | 12/1996 | Nakamaki ............ B29C 49/642 |
| | | | 425/526 |
| 2013/0029067 A1 | | 1/2013 | Dircx |
| 2015/0290423 A1 | | 10/2015 | Storbeck et al. |
| 2017/0035974 A1 | | 2/2017 | Berry et al. |
| 2017/0056603 A1 | | 3/2017 | Cowan et al. |
| 2018/0161496 A1 | | 6/2018 | Berry et al. |
| 2019/0233580 A1 | * | 8/2019 | Schiraldi ................. C08L 67/02 |
| 2021/0030950 A1 | | 2/2021 | Spohn et al. |
| 2022/0266490 A1 | * | 8/2022 | Hervet ................... B29B 11/14 |

FOREIGN PATENT DOCUMENTS

| | | |
|---|---|---|
| EP | 2727622 A1 | 5/2014 |
| WO | 2015066506 A2 | 5/2015 |
| WO | 2015164783 A1 | 10/2015 |
| WO | 2016172467 A1 | 10/2016 |
| WO | 2018075379 A1 | 4/2018 |
| WO | 2018075386 A1 | 4/2018 |
| WO | 2019152978 A1 | 8/2019 |
| WO | 2019161327 A1 | 8/2019 |

* cited by examiner

FLUID-CONTAINER AND METHOD FOR CONTROLLING CRYSTALLINITY IN BLOW-MOLDED CONTAINER

CROSS REFERENCE TO RELATED APPLICATIONS

This application is a U.S. national phase application under 35 U.S.C. § 371 of PCT International Application No. PCT/US2020/041968, filed 14 Jul. 2020, and claims the benefit of U.S. Provisional Patent Application No. 62/874,236, filed on 15 Jul. 2019, the disclosures of which are hereby incorporated by reference in their entirety herein.

BACKGROUND

Field of the Disclosure

The present disclosure is directed to systems and methods for controlling the crystallinity of material in a polymeric fluid container. The present disclosure is further directed to syringes for use in the medical field, such as to rolling diaphragm syringes. The present disclosure is also related to methods for controlling crystallinity in a polymeric material of a fluid container, including rolling diaphragm syringes. The present disclosure is further related to systems for controlling crystallinity of a polymeric material constituting a fluid container.

Description of Related Art

Polymeric materials (i.e., plastics) are ubiquitous, being used for fluid containers, packaging materials, articles of manufacture, sheeting, etc. The polymeric materials have physical properties associated with the crystallinity of the materials. For example, polymeric materials with amorphous polymeric structures tend to be translucent or transparent, flexible, soft, deformable, elastic, low heat resistance, and have a tendency to creep, whereas polymeric material with a more crystalline structure have generally opposite properties, tending to be rigid, high melting, strong, dense, opaque, and have lower creep. Amorphous polymers have low molecular structure and the polymeric chains have a high degree of disorder, allowing the chains greater ability to move relative to each other as the polymer is manipulated. As the crystalline structure of the polymer is increased, the chains become more ordered, where the polymeric chains begin to become locked into place as the polymer transitions from semi-crystalline structure to a more crystalline structure.

Crystallinity of an amorphous polymeric material may be increased by heating the material to above the glass transition temperature (Tg) where the polymer transitions from solid to being soft and pliable and then cooling the polymeric material to promote crystal growth within the polymeric structure. Heating is typically performed on the bulk polymer, for example using direct heating or infrared heating of the polymer, for example during a molding or extrusion process.

In many medical diagnostic and therapeutic procedures, a medical practitioner, such as a physician, injects a patient with one or more medical fluids. In recent years, a number of injector-actuated syringes and powered injectors for pressurized injection of medical fluids, such as a contrast solution (often referred to simply as "contrast" or "contrast medium"), a flushing agent, such as saline, and other medical fluids, have been developed for use in procedures such as computed tomography (CT), angiography, ultrasound, magnetic resonance imaging (MRI), positron emission tomography, and other imaging procedures. In general, these fluid injectors are designed to deliver a preset amount of fluid at a preset pressure and/or flow rate.

Typically, powered fluid injectors have at least one piston that is configured to connect to a plunger disposed within a syringe. The syringe generally includes a rigid barrel with the plunger being slidably disposed within the rigid barrel. The piston of the fluid injector drives the plunger in a distal direction relative to a longitudinal axis of the barrel to deliver the fluid from the syringe barrel and in the proximal direction to draw fluid into the syringe barrel.

The syringes and fluid paths used with powered fluid injectors are typically composed of a polymeric material. Syringes and fluid paths used in the medical field may be disposable and designed to be discarded after one use or may be multi-use over several fluid injection procedures when combined with certain safety features to prevent cross-contamination. Although fluid injector syringes are typically made by mass production methods such as injection molding using conventional polymeric materials, such syringes may require specific amounts of polymeric materials having desired properties, precision requirements in their manufacture, and the economic costs associated with packaging, shipping, and storage. The syringes may require different material properties in specific regions of the syringe body. One type of syringe that addresses various issues associated with conventional syringes is a rolling diaphragm syringe. Rolling diaphragm syringes, often times made of polyethylene terephthalate (PET), have a thin sidewall that is configured for rolling over upon itself when an end wall when interacting with a piston of a fluid injector. While rolling diaphragm-type syringes and containers may solve certain problems associated with conventional syringes, there is still room for improvement in polymeric rolling diaphragm syringes, other polymeric syringes, polymeric fluid containers, polymeric articles of manufacture, and polymeric packaging, as well as methods and systems related to the same.

BRIEF SUMMARY

These needs and others are met by various embodiments of the disclosed examples and aspects, which are directed to improved polymeric fluid containers and polymeric articles of manufacture, for example, a rolling diaphragm syringes and methods and systems for precisely and accurately controlling localized crystallinity of a polymeric material of the fluid container or article.

In a first embodiment of the present disclosure, a fluid container is provided. The fluid container has a proximal end having an end wall, a distal end having an open-ended neck, and a sidewall extending between the proximal end and the distal end along a longitudinal axis. A localized crystallinity of a polymeric material of the fluid container of at least a first region of the fluid container is greater than a crystallinity of a polymeric material of the fluid container of at least a second region. In certain embodiments, the fluid container may be a medical fluid container, such as a syringe, including a blow-molded rolling diaphragm syringe. In other embodiments, the fluid container may be a beverage container.

In another embodiment of the present disclosure, a method for controlling crystallinity of a polymeric material in a fluid container is provided. The method comprises injection molding the preform for the fluid container within an injection-mold, placing the preform into a blow-mold for blow-molding the fluid container, heating and injecting gas into the preform to cause the preform to expand against an inner surface of the blow-mold, thereby forming the rolling diaphragm syringe, and laser heating at least one localized portion of a polymeric material of the preform or the fluid container with at least one laser to above the glass transition temperature of the polymeric material to form a first localized crystalline region of the polymeric material, wherein the first localized crystalline region of the polymeric material has a crystallinity that is greater than a crystallinity in a portion of the preform or the fluid container that is not laser heated. In certain embodiments, the blow-molding process may include stretch blow-molding the preform. According to certain embodiments, laser heating at least one localized portion of a polymeric material of the preform or the fluid container with a laser may be performed on the preform in the injection-mold, in the blow-mold prior to heating and injecting gas into the preform (i.e., before blow-molding), in the blow-mold after heating but prior to stretch blow-molding, or in a separate apparatus before the heating and injecting gas step. In other embodiments, laser heating at least one localized portion of a polymeric material of the preform or the fluid container with a laser may be performed on the blow-molded rolling diaphragm syringe, either in the blow-mold after the heating and injecting step or in a separate apparatus. In still other embodiments, other polymer container forming technologies may be used instead of or in addition to blow-molding, such as injection molding, thin-walled injection molding, rotational molding, extrusion molding, forming (vacuum forming, thermoforming, reaction injection molding (RIM), etc.), 3-D printing, and combinations of any thereof.

In another embodiment of the present disclosure, a system for heating at least a portion of a fluid container is provided. The system may optionally comprise a fixture or mold having a profile shaped substantially the same as a profile of the preform of the fluid container (e.g., the preform may be laser heated while in a preform injection-mold after the injection molding process) or the profile of a blow-molded fluid container (e.g., the preform may be laser heated before the blow-molding process or the blow-molded fluid container may be laser heated in the blow-mold), and at least one laser positioned proximate to the fixture and oriented to laser heat at least one localized portion of a polymeric material of the preform or the blow-molded fluid container with the at least one laser to form at least one localized crystalline region of the polymeric material in the fluid container. The localized crystalline region of the polymeric material has a crystallinity that is greater than a crystallinity in a portion of the preform or the blow-molded fluid container that is not heated with the least one laser. In certain embodiments, the portions of the polymer that do not have increased crystallinity by heating with a laser above the glass transition temperature may still be heated by the laser but only to temperatures below the glass transition temperature of the polymer so that the polymeric region retains a more amorphous or semi-crystalline structure.

In another embodiment of present disclosure, a preform is provided. The preform comprises a proximal end, a distal end having an open-ended neck, and a sidewall extending between the proximal end and the distal end along a longitudinal axis. A crystallinity of a polymeric material of at least a first localized crystalline region of the preform is different than the crystallinity of the polymeric material of a second region of the preform.

In some examples or aspects of the present disclosure, systems for heating at least a portion of a fluid container are provided. The systems may comprise a fixture having a profile shaped substantially the same as a profile of the fluid container, and at least one laser positioned proximate to the fixture and structured to form at least one amorphous portion or localized crystalline portion in the fluid container. In still other embodiments, the structure of a polymeric material of an article of manufacture may have localized crystalline structure by laser heating at least a portion of the article of manufacture at a first region to provide a localized crystalline structure in at least the first region.

Other fluid containers, such as beverage bottles and the like, which may be formed by a blow-molding process may also allow selective control of crystallinity in the polymeric material according to the methods described herein.

Various other aspects of the present disclosure are recited in one or more of the following clauses:

Clause 1: A fluid container comprising: a proximal end having an end wall; a distal end having an open-ended neck; and a sidewall extending between the proximal end and the distal end along a longitudinal axis, wherein a localized crystallinity of a polymeric material of the fluid container of at least a first region of the fluid container is greater than a crystallinity of a polymeric material of the fluid container of at least a second region.

Clause 2: The fluid container of clause 1, wherein the polymeric material is selected from the group consisting of polyethylene terephthalate (PET), polyethylene terephthalate glycol (PETG), polyethylene (high density polyethylene (HDPE), low-density polyethylene (LDPE), and/or linear low density polyethylene (LLDPE)), polypropylene, polystyrene, polyvinyl chloride, polybutadiene, polyethylene oxide, poly(p-phenylene terephthalamide) (PPTA), polytetrafluoroethylene (PTFE), polyoxymethylene (POM), polybutylene terephthalate, polypropylene random copolymer, polypropylene impact copolymer, polypropylene homopolymer, acrylonitrile butadiene styrene (ABS), cyclic olefin polymer (COP), cyclic olefin copolymer (COC), multilayer polypropylene, polycarbonate, ethylene vinyl acetate (EVA), nylon 6, nylon 8, nylon 12, nylon 6,6, nylon 6,10, and co-polymers or mixtures/layers of any thereof.

Clause 3: The fluid container of clause 1 or 2, wherein the polymeric material is polyethylene terephthalate Clause 4: The fluid container of clause 1 or 2, wherein the polymeric material is a multi-layer material comprising at least one layer of polymeric material selected from the group consisting of polyethylene terephthalate (PET), polyethylene terephthalate glycol (PETG), polyethylene (high density polyethylene (HDPE), low-density polyethylene (LDPE), and/or linear low density polyethylene (LLDPE)), polypropylene, polystyrene, polyvinyl chloride, polybutadiene, polyethylene oxide, poly(p-phenylene terephthalamide) (PPTA), polytetrafluoroethylene (PTFE), polyoxymethylene (POM), polybutylene terephthalate, polypropylene random copolymer, polypropylene impact copolymer, polypropylene homopolymer, acrylonitrile butadiene styrene (ABS), cyclic olefin polymer (COP), cyclic olefin copolymer (COC), multilayer polypropylene, polycarbonate, ethylene vinyl acetate (EVA), nylon 6, nylon 8, nylon 12, nylon 6,6, nylon 6,10, and copolymers or mixtures/layers of any thereof.

Clause 5: The fluid container of any of clauses 1 to 4, wherein at least portion of at least the first region is on the end wall of the fluid container.

Clause 6: The fluid container of any of clauses 1 to 4, wherein at least portion of at least the first region is on the sidewall of the fluid container.

Clause 7: The fluid container of any of clauses 1 to 4, wherein at least portion of at least the first region is on the distal end of the fluid container.

Clause 8: The fluid container of any of clauses 1 to 7, wherein the fluid container is a syringe.

Clause 9: The fluid container of clause 8, wherein the syringe is a rolling diaphragm syringe, wherein at least a portion of the sidewall is flexible such that the sidewall rolls upon itself with an outer surface of the sidewall at a folding region being folded in a radially inward direction when acted upon by an external force in a direction from the proximal end toward the distal end, and wherein the sidewall unrolls with the outer surface of the sidewall at the folding region being unfolded in a radially outward direction when acted upon by the external force in a direction from the distal end toward the proximal end.

Clause 10: The fluid container of any of clauses 1 to 9, wherein the localized crystallinity of at least the first region is in the form of one or more of letters, numbers, images, barcodes, or other indicia on the first region of the fluid container.

Clause 11: The fluid container of any of clauses 1 to 10, wherein the localized crystallinity of the fluid container changes at least one material property of the polymeric material of at least the first region.

Clause 12: The fluid container of clause 11, wherein the at least one material property is selected from the group consisting of opacity, rigidity, flexibility, brittleness, softness, strength, coefficient of friction, stretch, gas permeability, and combinations of any thereof.

Clause 13: A method for locally controlling crystallinity of a polymeric material in a fluid container, the method comprising: injection molding the preform for the fluid container within an injection-mold; placing the preform into a blow-mold for blow-molding the fluid container; heating and injecting gas into the preform to cause the preform to expand against an inner surface of the blow-mold, thereby forming the fluid container; and laser heating at least one localized portion of a polymeric material of the preform or the fluid container with at least one laser to above the glass transition temperature of the polymeric material to form a first localized crystalline region of the polymeric material, wherein the first localized crystalline region of the polymeric material has a crystallinity that is greater than a crystallinity in a portion of the preform or the fluid container that is not laser heated.

Clause 14: The method of clause 13, wherein the fluid container is a syringe.

Clause 15: The method of clause 13, wherein the fluid container is a rolling diaphragm syringe, wherein at least a portion of the sidewall is flexible such that the sidewall rolls upon itself with an outer surface of the sidewall at a folding region being folded in a radially inward direction when acted upon by an external force in a direction from the proximal end toward the distal end, and wherein the sidewall unrolls with the outer surface of the sidewall at the folding region being unfolded in a radially outward direction when acted upon by the external force in a direction from the distal end toward the proximal end.

Clause 16: The method of any of clauses 13 to 15, wherein the localized crystallinity of at least the first region is in the form of one or more of letters, numbers, images, barcodes, or other indicia on the first region of the fluid container.

Clause 17: The method of any of clauses 13 to 16, wherein the polymeric material comprises polyethylene terephthalate.

Clause 18: The method of any of clauses 13 to 17, wherein the polymeric material comprises a multi-layered polymeric material and wherein heating at least one localized portion of a polymeric material further comprises: heating one or more layer of the multi-layer polymeric material with the at least one laser according to laser depth focus, laser light wavelength, and combinations thereof.

Clause 19: A system for heating at least a portion of a fluid container, the system comprising: a fixture having a profile shaped substantially the same as a profile of a preform of the fluid container or the profile of a blow-molded fluid container; and at least one laser positioned proximate to the fixture and oriented to laser heat at least one localized portion of a polymeric material of the preform or the blow-molded fluid container with the at least one laser to form at least one localized crystalline region of the polymeric material in the fluid container, wherein the localized crystalline region of the polymeric material has a crystallinity that is greater than a crystallinity in a portion of the preform or the blow-molded fluid container that is not heated with the least one laser.

Clause 20: A preform for blow-molding a container, the preform comprising: a proximal end; a distal end having an open-ended neck; and a sidewall extending between the proximal end and the distal end along a longitudinal axis, wherein a crystallinity of a polymeric material of at least a first localized crystalline region of the preform is different than the crystallinity of the polymeric material of a second region of the preform.

Clause 21. A beverage container comprising: a proximal end having an end wall; a distal end having an open-ended neck; and a sidewall extending between the proximal end and the distal end along a longitudinal axis, wherein a localized crystallinity of a polymeric material of the beverage container of at least a first region of the beverage container is greater than a crystallinity of a polymeric material of the beverage container of at least a second region.

Clause 22. The beverage container of clause 21, wherein the beverage container has a reduced gas permeation at at least the first region of the beverage container.

Further details and advantages of the various examples described in detail herein will become clear upon reviewing the following detailed description of the various examples in conjunction with the accompanying drawing figures.

DETAILED DESCRIPTION OF THE DISCLOSURE

Figure 1A:
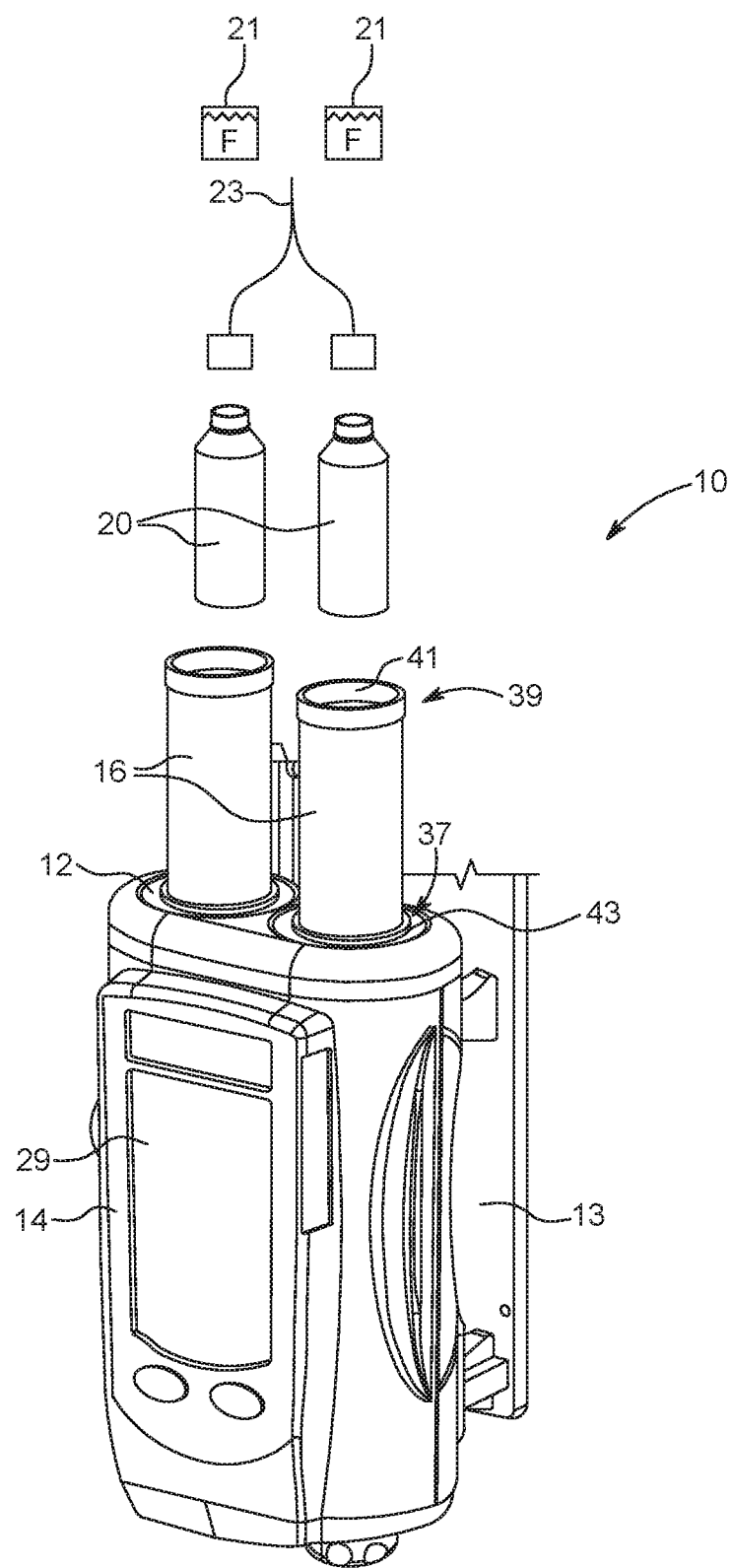
FIG. 1A is a front perspective view of a fluid injector and a rolling diaphragm syringe for use therewith in accordance with some examples or aspects of the present disclosure.

The illustrations generally show preferred and non-limiting examples or aspects of the systems and methods of the present disclosure. While the description presents various examples or aspects of the devices, it should not be interpreted in any way as limiting the disclosure. Furthermore, modifications, concepts, and applications of the disclosure's examples or aspects are to be interpreted by those skilled in the art as being encompassed by, but not limited to, the illustrations and descriptions herein.

The following description is provided to enable those skilled in the art to make and use the described examples or aspects contemplated for carrying out the disclosure. Various modifications, equivalents, variations, and alternatives, however, will remain readily apparent to those skilled in the art. Any and all such modifications, variations, equivalents, and alternatives are intended to fall within the spirit and scope of the present disclosure. For example, while various examples herein are described in reference to a fluid container, such as a medical syringe and more specifically to a rolling diaphragm type syringe, the present disclosure is no limited to fluid containers and may be applied to other polymeric or plastic articles of manufacture, including, but not limited to, water or beverage bottles and other commercial fluid containers, plastic packaging, such as clam-shell packaging, plastic films, plastic sheets, 3-D printed polymeric articles, polymeric materials formed by other article manufacturing methods (injection molding, thin-walled injection molding) extrusion molding, vacuum forming, thermoforming, reaction injection molding (RIM), rotational molding, etc.), and other plastic materials made from a polymer that can have its crystallinity changed by heating above the glass transition temperature.

For purposes of the description hereinafter, the terms "upper", "lower", "right", "left", "vertical", "horizontal", "top", "bottom", "lateral", "longitudinal", and derivatives thereof shall relate to the disclosure as it is oriented in the drawing figures. When used in relation to a rolling diaphragm syringe, the term "proximal" refers to a portion of a rolling diaphragm syringe nearest to a fluid injector when a rolling diaphragm syringe is oriented for connecting to a fluid injector. When used in relation to a rolling diaphragm syringe, the term "distal" refers to a portion of a rolling diaphragm syringe farthest away from a fluid injector when a rolling diaphragm syringe is oriented for connecting to a fluid injector.

When used in relation to a rolling diaphragm syringe, the term "radial" refers to a direction in a cross-sectional plane normal to a longitudinal axis of a rolling diaphragm syringe extending between proximal and distal ends. When used in relation to a rolling diaphragm syringe, the term "circumferential" refers to a direction around an inner or outer surface of a sidewall of a rolling diaphragm syringe. When used in relation to a rolling diaphragm syringe, the term "axial" refers to a direction along a longitudinal axis of a rolling diaphragm syringe extending between the proximal and distal ends.

The term "flexible", when used in connection with a rolling diaphragm syringe, means that at least a portion of a rolling diaphragm syringe, such as a sidewall of a rolling diaphragm syringe, is capable of bending or being bent to change a direction in which it extends. The terms "roll over", "rolling over", and "rolls upon itself", when used in connection with a rolling diaphragm syringe, refer to an ability of a first portion of a rolling diaphragm syringe, such as a proximal portion of a sidewall of a rolling diaphragm syringe, to bend approximately 18a relative to a second portion of a rolling diaphragm syringe, such as a distal portion of a sidewall of a rolling diaphragm syringe, when urged by a piston of a fluid injector or a rolling fixture.

As used herein, the term "crystallinity" as related to a polymeric material refers to at least partial alignment of at some of the polymeric molecular chains within the polymeric structure. The molecular chains of a polymer that has a first crystallinity, such as a more ordered crystallinity, shall be more folded together and/or aligned and form ordered regions called lamellae, which may compose larger spheroidal structures. More crystalline crystallinity may also be characterized by having a greater number of parallel and closely packed polymer chains, whereas amorphous may be characterized by having more disordered and random polymer chains. The degree of crystallinity may be estimated by different analytical methods and may range between 10 and 80%, with crystallized polymers often called "semi-crystalline." The properties of semi-crystalline polymers are determined not only by the degree of crystallinity, but also by the size and orientation of the molecular chains. As used herein, the term "amorphous" as related to a polymeric material refers to less alignment and a more random orientation of the polymeric chains within the polymeric structure. Typically, polymeric materials with more crystalline structures have more highly packed polymer chains increasing the strength and rigidity of the material and are generally less transparent, whereas polymeric materials with a more amorphous structure have randomly ordered polymeric chains and have lower strength, are more flexible, and are generally more transparent compared to polymeric material with higher crystallinity.

It is to be understood, however, that the disclosure may assume alternative variations and step sequences, except where expressly specified to the contrary. It is also to be understood that the specific devices and processes illustrated in the attached drawings, and described in the following specification, are simply exemplary aspects of the disclosure. Hence, specific dimensions and other physical characteristics related to the examples disclosed herein are not to be considered as limiting.

As used herein, the term "at least one of" is synonymous with "one or more of." For example, the phrase "at least one of A, B, and C" means any one of A, B, and C, or any combination of any two or more of A, B, and C. For example, "at least one of A, B, and C" includes one or more of A alone; or one or more B alone; or one or more of C alone; or one or more of A and one or more of B; or one or more of A and one or more of C; or one or more of B and one or more of C; or one or more of all of A, B, and C. Similarly, as used herein, the term "at least two of" is synonymous with" two or more of "For example, the phrase "at least two of D, E, and F" means any combination of any two or more of D, E, and F. For example, "at least two of D, E, and F" includes one or more of D and one or more of E; or one or more of D and one or more of F; or one or more of E and one or more of F; or one or more of all of D, E, and F.

Various embodiments of the present disclosure are directed to polymeric articles of manufacture having one or more regions with localized crystallinity of a polymeric material, that is, where the crystallinity of the one or more regions of the polymer is greater than the crystallinity of the polymeric material at at least a second region of the article of manufacture. In certain embodiments, the article of manufacture may be a fluid container, such as but not limited to a commercial beverage container or a medical fluid container. Examples of medical fluid containers can include bottles, bags, vials, and syringes, including for example rolling diaphragm syringes, as will be described in detail as an exemplary embodiment herein. Other article of manufacture suitable for increasing localized crystallinity of the polymeric material include, for example, plastic packaging, such as clam-shell packaging, plastic films, plastic sheets, 3-D printed polymeric articles, polymeric materials formed by other article manufacturing methods (injection molding, thin-walled injection molding) extrusion molding, vacuum forming, thermoforming, reaction injection molding (RIM), rotational molding, etc.), and other plastic materials made from a polymer that can have its crystallinity changed by heating above the glass transition temperature.

According to certain embodiments, the fluid container may be a commercial beverage container, such as a water bottle, soda bottle, alcoholic beverage bottle, milk bottle, or other beverage container. According to these embodiments, increasing the localized crystallinity of at least a first region of the beverage container using the laser heating methods described herein may improve at least one material property of the polymeric material of the beverage container. For example, according to embodiments, the increased crystallinity may make the at least one region structurally stronger compared to a region that does not include the localized crystallinity. The structurally stronger region may increase the regions ability to handle higher pressures in the zone, such as an increased pressure due to a pressurized gas, for example in a carbonated beverage bottle. In particular embodiments, the region with the increased localized crystallinity may be at least a portion of the base or end wall, the sidewall, and/or the distal conical area adjacent to the fluid outlet. According to other embodiments, the increased crystallinity may make the at least one region less permeable to gas, for example with a carbonated beverage container, thereby increasing a carbonation shelf-life of the carbonated beverage. In still other embodiments, increasing the strength of the at least one region may allow for a lighter weight fluid bottle that incorporates thinner wall thicknesses while still maintaining the structural rigidity, so that the beverage container does not collapse under its own weight during manufacture or storage; or during use (i.e., while a user drinks directly from the bottle)

Polymeric materials that may be suitable for use according to various embodiments described herein, include, for example, plastics selected from polyethylene terephthalate (PET), polyethylene terephthalate glycol (PETG), polyethylene (high density polyethylene (HDPE), low-density polyethylene (LDPE), and/or linear low density polyethylene (LLDPE)), polypropylene, polystyrene, polyvinyl chloride, polybutadiene, polyethylene oxide, poly(p-phenylene terephthalamide) (PPTA), polytetrafluoroethylene (PTFE), polyoxymethylene (POM), polybutylene terephthalate, polypropylene random copolymer, polypropylene impact copolymer, polypropylene homopolymer, acrylonitrile butadiene styrene (ABS), cyclic olefin polymer (COP), cyclic olefin copolymer (COC), multilayer polypropylene, polycarbonate, ethylene vinyl acetate (EVA), nylon 6, nylon 8, nylon 12, nylon 6,6, nylon 6,10, and co-polymers or mixtures/layers of any thereof. In specific embodiments, the polymeric material may be polyethylene terephthalate (PET).

According to other embodiments, the polymeric material may be a multi-layer material, wherein at least one of the layers is a polymeric material selected from polyethylene terephthalate (PET), polyethylene terephthalate glycol (PETG), polyethylene (high density polyethylene (HDPE), low-density polyethylene (LDPE), and/or linear low density polyethylene (LLDPE)), polypropylene, polystyrene, polyvinyl chloride, polybutadiene, polyethylene oxide, poly(p-phenylene terephthalamide) (PPTA), polytetrafluoroethylene (PTFE), polyoxymethylene (POM), polybutylene terephthalate, polypropylene random copolymer, polypropylene impact copolymer, polypropylene homopolymer, acrylonitrile butadiene styrene (ABS), cyclic olefin polymer (COP), cyclic olefin copolymer (COC), multilayer polypropylene, polycarbonate, ethylene vinyl acetate (EVA), nylon 6, nylon 8, nylon 12, nylon 6,6, nylon 6,10, and co-polymers or mixtures or layers of any thereof. Multi-layered polymers may include multi-layer films, multi-layer components and articles, multi-layer blow molding, such as in a form fill seal process, multi-layer extrusion compositions and articles, and combinations thereof.

According to various embodiments comprising a multi-layered structure, one or more regions of one or more of the polymeric material layers may have increased localized crystallinity relative to other regions of the one or more polymeric material layers. As will be described herein, the increased localized crystallinity of the localized portion of the polymeric material (whether in a solid polymeric structure or as one or more layers in a multi-layered structure) may be formed by localized heating of the portion or region to be crystallized by heating with a laser to above the glass transition temperature of the polymeric material. Such heating above the glass transition temperature may change the structural arrangement of the polymeric chains in the material forming a more crystalline structure relative to the regions that have not been laser heated. The increased localized crystallinity of the region may be semi-crystalline or crystalline in the laser heated region. Heating with a laser allows directed and accurate heating of small regions of the polymeric material. Further, in embodiments where the polymeric material is a multi-layered polymeric material or alternatively, a polymeric material having a relatively thick cross-section, localized heating with a laser may allow focused heating of specific layers of the multi-layered material or focused heating of a near surface, a far surface of an interior of a thick polymeric material structure. Such focused laser heating may be accomplished by the at least one laser according to laser depth focus, laser light wavelength (e.g., laser light having a wavelength that selectively heats a particular polymeric material layer in the multi-layered polymer), and combinations thereof.

Increasing the localized crystallinity of one or more regions of the polymeric material may change at least one material property of the polymeric material within the crystallized region. For example, increasing the crystallinity of a local region of a polymeric material may change (increase or decrease) a property selected from increased opacity, increased rigidity, flexibility, brittleness, decreased softness, increased strength, decreased coefficient of friction, decreased stretch, decreased gas permeability, or combinations of any thereof of polymeric material relative to other regions of the polymeric material that have not been laser heated.

In certain embodiments, the laser heating and controlled crystallization may be used to form symbols and other indicia on a surface of or in the interior of the plastic structure. For example, according to various embodiments, the localized crystalline region may have a different opacity than the non-crystalline regions. That is, the more crystalline regions may be opaque or clouded relative to a nearby less crystalline region. Using a laser directed heating process, the crystalline regions may be in the form of letters, numbers, images, brand logos, bar codes, indicators (such as fluid volume or prior use indicators), or combinations thereof. Such an approach may save on labeling costs and also provide indicia that is permanently formed as part of the polymeric structure that cannot be removed, smear, become unreadable, be counterfeited, or otherwise rub off. According to these embodiments, since the image is part of the polymeric structure of the article, it provides a smooth surface compared to marking processes which rely of printing on or etching the polymeric material and further, cannot contaminate a fluid or material container within a polymeric container.

While the various embodiments directed to a rolling diaphragm syringe described herein are discussed with blow-molded containers and the injection molded preforms that are used in the blow-molding process, other plastic molding methodologies may also be suited to increasing the localized crystallinity of one or more specific regions of the polymeric materials, as described herein. Other suitable polymer forming technologies that may be utilized or are suitable for the processes described herein include, for example, injection molding, thin-walled injection molding, extrusion, vacuum forming, thermoforming, reaction injection molding, rotational molding, 3-D printing, and combinations thereof. According to these embodiments, the described laser heating of specific regions of the polymeric material may be affected before, during, and/or after the specific polymer forming process. According to other embodiments, an article of manufacture that has been machined to a particular shape or structure and then annealed may be treated with the laser heating and localized crystallization as described herein.

For example, in a 3-D printing process wherein an article of manufacture is created using a polymeric 3-D printing process, specific regions of the developing 3-dimensional polymeric structure may be irradiated by laser light as the polymer is printed on the developing structure or in other embodiments, the polymeric structure may be irradiated by the laser light at some time after the region is printed, for example, after the 3-dimensional structure is complete or a portion of the 3-dimensional structure has been completed. According to one embodiment, the 3-D printer may include a laser attached at or near the polymer nozzle that selectively irradiates the polymeric material as particular regions of the final structure are printed onto the developing structure, either during the curing process or a short time after the polymeric material has cured. In other embodiments, the laser may be located at a different region of the 3-D printer and the laser may selectively irradiate regions of the structure after the polymer has been printed and cured. Thus, the 3-D printed article may have specific localized regions with high crystallinity and other regions with lower crystallinity.

According to various embodiments, plastic articles of manufacture, such as polymer sheets or packaging films (such as for clam-shell or blister-pack packaging) may be laser heated at specific regions to control the localized crystalline structure of the polymeric material. The laser heating may be performed at any reasonable time during the manufacturing process.

Specific embodiments of articles with localized crystallinity will be enabled by reference to an exemplary embodiment comprising a rolling diaphragm syringe having a PET polymeric structure formed by a stretch blow-molding process from an injection molded preform. While this exemplary embodiments described specifically the disclosure with reference to a single article, it is to be understood that the disclosure is not limited to use with a rolling diaphragm syringe.

Blow-molding containers, such as a rolling diaphragm syringe, generally involves injecting gas into a heated (or pre-heated) preform made by an injection-molding process and may involve a suitable polymeric material that may be polyethylene terephthalate ("PET"). PET raw resin typically in a more crystalline form, often appearing white or translucent in color, before an injection-molding operation is performed. Blow-molding may involve stretch blow-molding where a stretch member is inserted into the interior of the blow-molded container to stretch the polymer during the blow-molding process. When a blow molding preform is made by injection molding, the resultant polymeric material that was initially more crystalline becomes more amorphous, by virtue of the polymeric material exceeding its melting temperature, which may be about 260° C. for PET. PET and various other polymeric materials having greater amorphous structure may generally display more transparency, appearing as a clear polymeric material. Known injection molded PET syringes are generally considered amorphous or semi-crystalline with readings typically below 10% crystallinity, wherein percent crystallinity is defined herein the ratio of crystalline material to total polymeric material (crystalline material+amorphous material) (e.g., most polymers exist as complex structures made up of both crystalline and amorphous regions).

As will be discussed herein, in accordance with various disclosed embodiments, a rolling diaphragm syringe may have localized crystalized regions having greater than 30% crystallinity. This may be achieved in PET syringes by heating the localized regions above the glass transition temperature of the PET, e.g., greater than 70° C., but less than the melting temperature of PET. These regions may appear translucent white in color, crystalline, stiff, strong, and hard, as compared to more transparent or clear regions that have less than 30% crystallinity. Additionally, localized regions of a syringe may have deliberate amorphous regions wherein at least a portion of a crystalline region are heated to a temperature greater than the melting temperature and melted, making the material, for example, amorphous and clear in color, after being blown, to make the regions more flexible, as compared to adjacent regions having a more crystalline polymeric structure.

Moreover, in accordance with various embodiments of this disclosure, typically there are two types of crystals that may be formed during a blow molding process. For example, heat induced crystallinity forms large crystals that may turn white or opaque. This may typically start above the glass transition temperature for a material (e.g., greater than 70° C. for PET). Additionally, stretching the PET during the blow molding process also creates small crystals that generally are clear. Typically, if the percent crystallinity gets above 30%, then the PET starts to turn translucent, and then white. Blow-molding, including stretch blow-molding typically involves heating the polymeric article preform prior to stretching. Conventional heating processes may include infrared heating of the preform either before insertion of the preform into the blow-mold or heating within the blow-mold. According to various embodiments herein, heating the preform prior to blow-molding may be performed broadly by heating with a laser over a broad area, either alone or in combination with another heating mechanism, such as an infrared heater. Once the preform has been broadly heated with the laser, a more focused and precise laser heating step to above the glass transition temperature may occur to achieve the desired targeted crystalline regions.

With reference to FIG. 1A, a fluid injector 10 includes at least one injector head 12 and an injector housing 14. In some examples or aspects, such as shown in FIG. 1A, the fluid injector 10 may include two injector heads 12 arranged in a side-by-side or any other orientation. Each injector head 12 may be formed at a front end 43 of the injector housing 14 and may be configured for receiving and retaining at least one pressure jacket 16. Examples of suitable front-loading fluid injectors that may be used or modified for use with the herein-described system, including at least one pressure jacket 16 and a rolling diaphragm syringe 20, are disclosed in International Application Publication Nos. WO 2015/164783 and WO 2016/172467, the disclosures of which are incorporated herein by reference. While FIG. 1A illustrates the fluid injector 10 with two injector heads 12, each with a corresponding pressure jacket 16, other examples of the fluid injector 10 may include a single injector head 12 and a corresponding pressure jacket 16 or more than two injector heads 12 with a corresponding number of pressure jackets 16.

Each injector head 12 includes a piston, such as a reciprocally driven piston (not shown) moved by a motor (not shown) which is operated by a controller (not shown). Each piston may be configured to extend into and from the respective injector head 12 through an opening 37 in the front end 43 of the injector housing 14. The pistons impart a motive force to at least a portion of rolling diaphragm syringes 20, for example the end wall, disposed in the respective pressure jackets 16, as described herein. The syringe 20 may include a piston engagement portion 81 for releasably engaging a piston of an injector head 12. Examples of piston mechanisms for engaging a piston engagement portion 81 are described in International Application Publication Nos. WO 2018/075379 and WO 2018/075386, the disclosures of which are incorporated herein in their entirety.

With continued reference to FIG. 1A, the fluid injector 10 is configured to receive a rolling diaphragm syringe 20 within each pressure jacket 16. The pressure jacket 16 is typically a reusable or a multi-use component, while the rolling diaphragm syringe 20 may be a single-use component. In some embodiments, the rolling diaphragm syringe 20 may be a multi-use component.

Figure 1B:
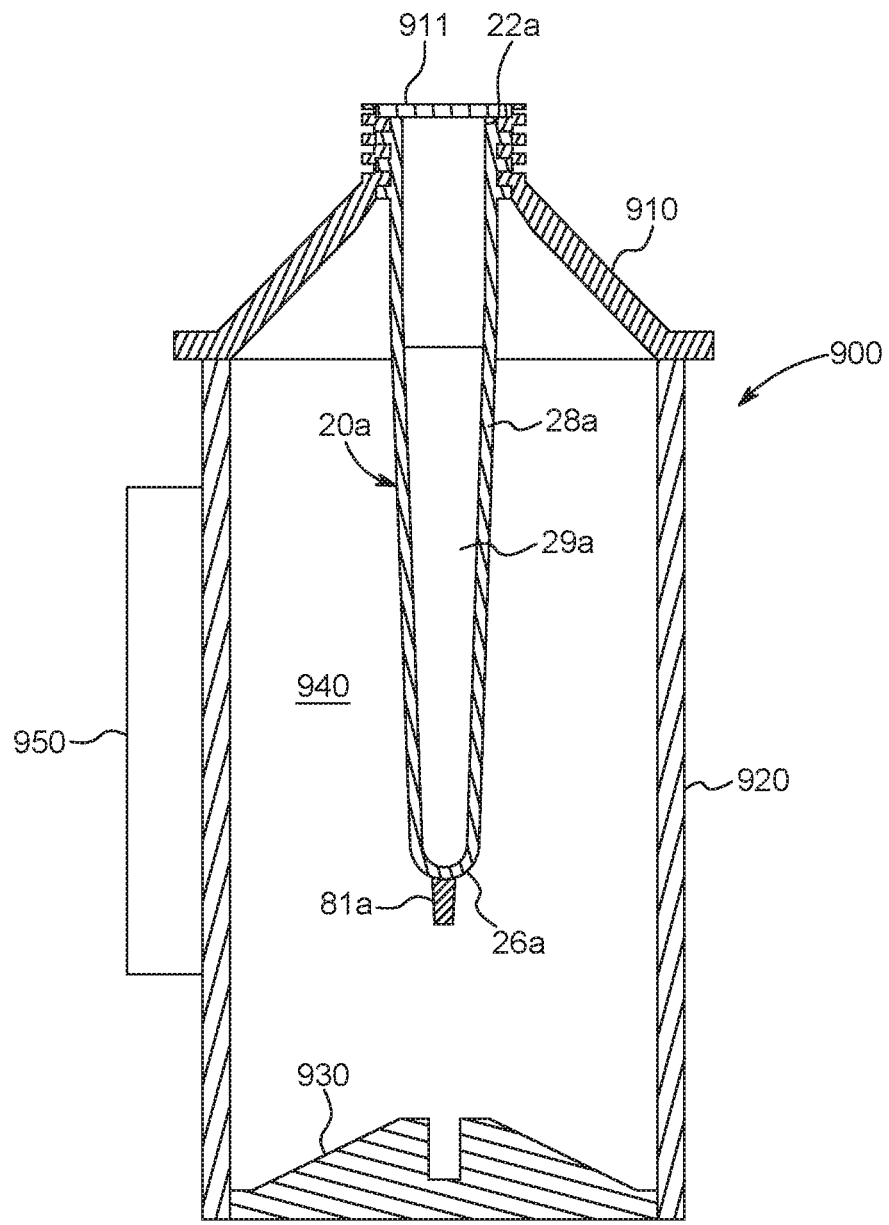
FIG. 1B is a side view of a cross-sectional view of a syringe preform in a mold die according to another example or aspect of the disclosure.

In various embodiments, the rolling diaphragm syringe 20 is formed by a stretch blow-molding process in which an injection-molded preform is elongated and enlarged by a combination of heating and stretching using a metal core and/or radial expansion by air pressure. An exemplary stretch blow molding process is described in International Patent Application Publication No. WO 2015/066506, the disclosure of which is incorporated herein by reference in its entirety. A stretch blow-molding and annealing process generally includes manipulating a syringe preform 20a, shown in FIG. 1B, to produce the desired shape of the fully formed rolling diaphragm syringe 20 shown in FIG. 1A. The syringe preform 20a, as shown in FIG. 1B, may be produced from a process such as injection-molding. The syringe preform 20a includes a distal end 22a and an expandable body having a cylindrical sidewall 28a, an interior volume 29a defined by the sidewall 28a, and a proximal end 26a which may have a piston engagement portion 81a attached thereto. In certain embodiments, at least a portion of the distal end 22a of the syringe preform 20a may have substantially the same shape as a corresponding portion of the distal end 22 of the fully formed rolling diaphragm syringe 20 illustrated in FIGS. 2 and 3. In such embodiments, at least a portion of the distal end 22a of the syringe preform 20a is substantially unchanged during stretch blow molding process.

As shown in FIG. 1B, the syringe preform 20a has been inserted into a mold die 900. The mold die 900 may include a distal section 910, a middle section 920, and a proximal section 930, corresponding to the distal end, the central sidewall, and the proximal end wall of the syringe, which together define a mold cavity 940. At least a portion of the syringe preform 20a may be expanded to adopt the shape of the mold cavity 940. In some embodiments, a stretch rod may be inserted through opening 911 of the mold die 900 and distal end 22a into the interior volume 29a of the syringe preform 20a. The stretch rod may be advanced towards the rear section 930 of the cavity to axially stretch the sidewall 28a and/or the proximal end 26a towards the rear section 930 during the stretching portion of the stretch blow-molding process.

In certain embodiments, the internal volume 29a of the syringe preform 20a may be pressurized to expand the sidewall 28a and the proximal end 26a axially and/or radially towards the middle section 920 and the rear section 930 of the mold die 900. Pressurizing the internal volume 29a may be achieved by supplying pressurized fluid, such as air or another gas, into the internal volume 29a and/or by generating a vacuum in the mold cavity 940 outside the internal volume 29a. In various embodiments, internal volume 29a may be pressurized to up to 500 psi. In certain embodiments, internal volume 29a may be pressurized to up to 100 psi.

The syringe preform 20a is heated to increase its pliability. As shown in FIG. 1B, a heat source 950 may be provided on the mold die 900 to generate heat and increase the temperature of the mold die 900, gas within the mold cavity 940, and/or the syringe preform 20a. In particular, heat may be transferred from the heat source 950 to the mold die 900, gas within the mold cavity 940, and/or the syringe preform 20a via convection, conduction, and/or radiation.

Figure 2:
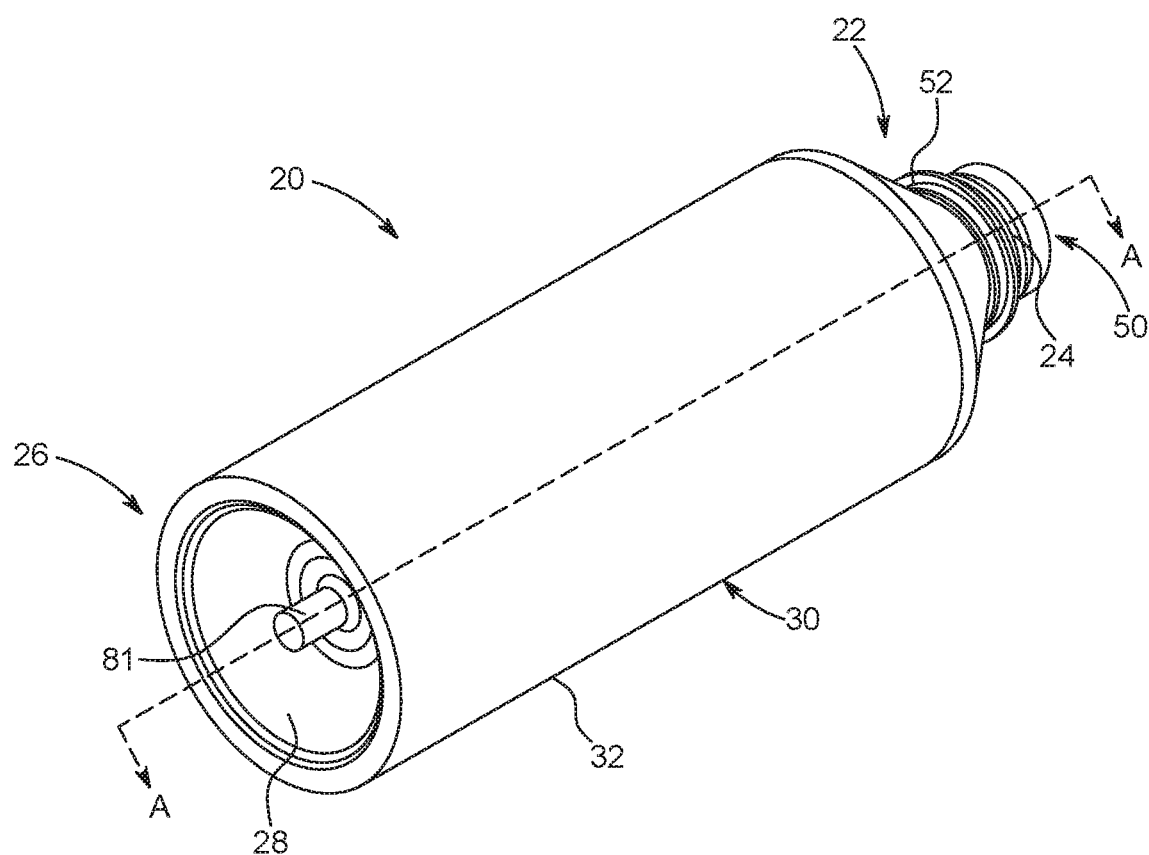
FIGS. 2 and 3 illustrate an example of a rolling diaphragm syringe in a completely unrolled configuration, including a perspective view (FIG. 2) and a cross sectional view (FIG. 3) taken along line A-A of FIG. 2.
Figure 3:
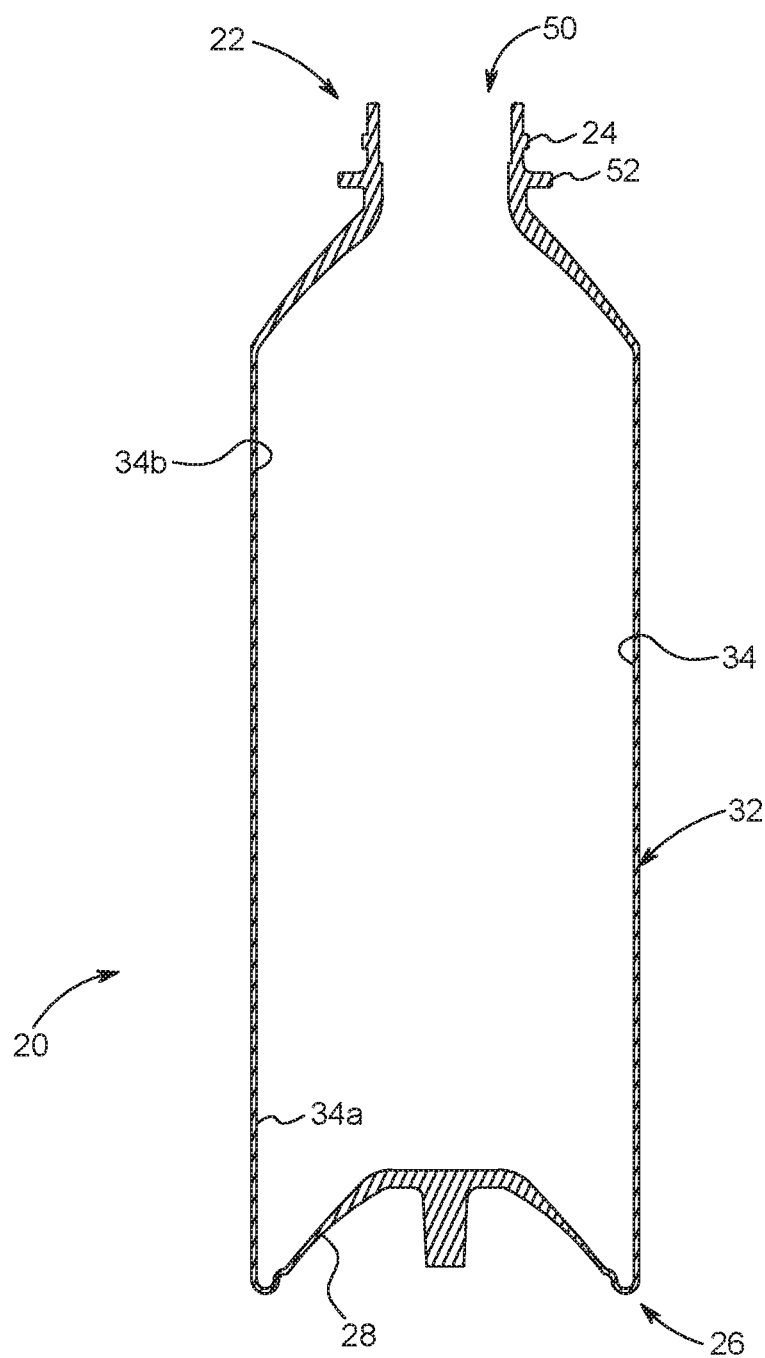
Figure 4:
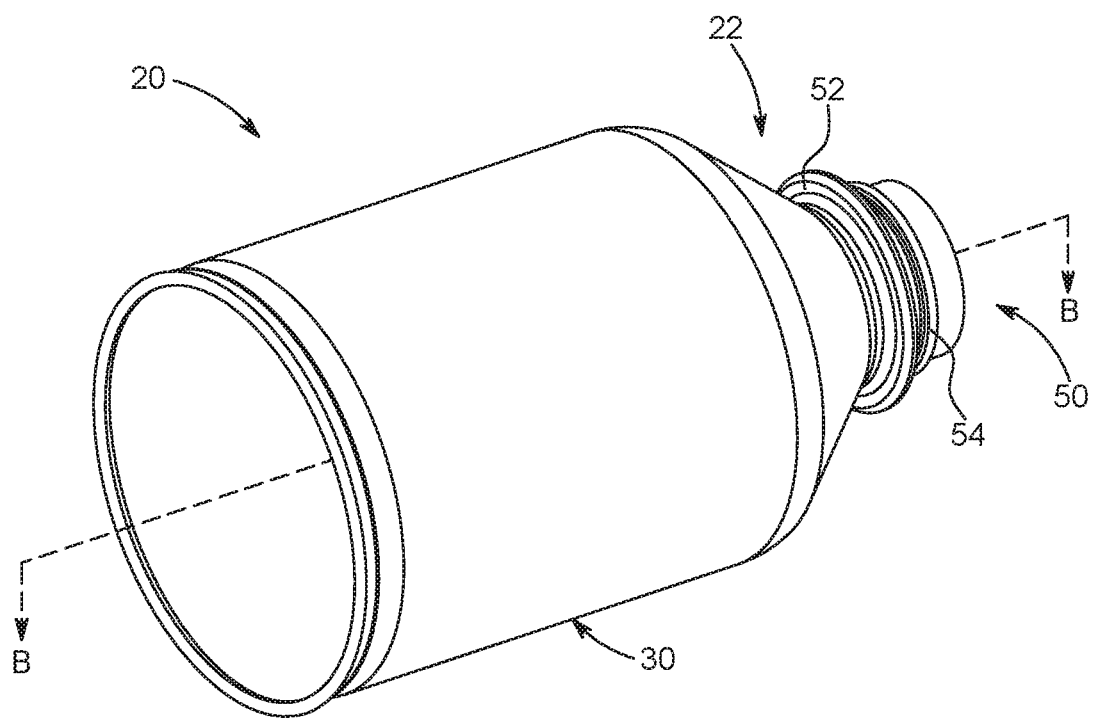
FIGS. 4 and 5 illustrate the rolling diaphragm syringe in a rolled configuration, including a perspective view (FIG. 4) and a cross sectional view (FIG. 5) taken along line B-B of FIG. 4.

As a result of expansion on the syringe preform 20a within the mold cavity 940, the syringe preform 20a adopts substantially the same shape of the fully formed rolling diaphragm syringe 20 shown in FIGS. 2 and 3. Accordingly, the expanded syringe preform 20a generally adopts the internal shape of the mold die 900, which corresponds to the shape of the fully formed rolling diaphragm syringe 20.

The syringe preform 20a may subsequently be heated and/or reheated to anneal or otherwise alter the molecular structure of the syringe preform 20a. In some examples or aspects, this may occur while the syringe preform 20a is still within the mold die 900. The heat source 950 may be utilized to provide a constant or fluctuating level of heat for annealing the syringe preform 20a. In some examples or aspects, the heating of the syringe preform 20a may be above a glass transition temperature of the material (e.g. polypropylene random copolymer, polypropylene impact copolymer, polypropylene homopolymer, polypropylene, PET, POM, ABS, HPDE, LDPE, LLDPE, multilayer polypropylene, polycarbonate, ethylene vinyl acetate, polyethylene, PETG, polystyrene, polyvinyl chloride, polybutadiene, polyethylene oxide, PPTA, PTFE, polybutylene terephthalate, polypropylene random copolymer, polypropylene impact copolymer, polypropylene homopolymer, COP, COC, polycarbonate, nylon 6, nylon 8, nylon 12, nylon 6,6, nylon 6,10, and/or the like) forming the syringe preform 20a.

In some examples or aspects, the mold die 900 may be cooled, either passively or via a forced cooling system, prior to removal of the fully formed rolling diaphragm syringe 20. In some examples or aspects, after removal of the rolling diaphragm syringe 20 from the mold die 900, a post-molding procedure may be performed on the rolling diaphragm syringe 20. Examples of post-molding procedures include but are not limited to an initial rolling of the syringe 20 as described, for example, in International Application No. PCT/US2019/018404, the disclosure of which is incorporated herein by reference in its entirety.

With reference to FIGS. 2 and 3, the rolling diaphragm syringe 20 generally includes a hollow body defining an interior volume and which includes a distal end 22 including a discharge neck 24 having a fluid outlet 50, a proximal end 26 having a closed end wall 28, and a flexible sidewall 30 having an outer surface 32 and an inner surface 34 (see FIG. 3) extending therebetween. The syringe 20 can be any suitable length, which can be determined either by the length of the sidewall 30 and/or by the extent that the rolling diaphragm has been rolled and can have any interior volume depending on the length, the diameter, the fluid volume being injected and/or the size of fluid injector being used. The syringe 20 may include a retention flange 52 located on the discharge neck 24 to assist in retaining the syringe 20 in the injector and pressure jacket during a pressurized injection procedure.

The rolling diaphragm syringe 20 may be made of any suitable medical-grade plastic or polymeric material, such as, but not limited to, polypropylene random copolymer, polypropylene impact copolymer, polypropylene homopolymer, polypropylene, PET, POM, ABS, HPDE, nylon, cyclic olefin copolymer, multilayer polypropylene, polycarbonate, ethylene vinyl acetate, polyethylene, and the like. The material of the rolling diaphragm syringe 20 may be selected to meet the required tensile and planar stress requirements, water vapor transmission, and chemical/biological compatibility.

Figure 5:
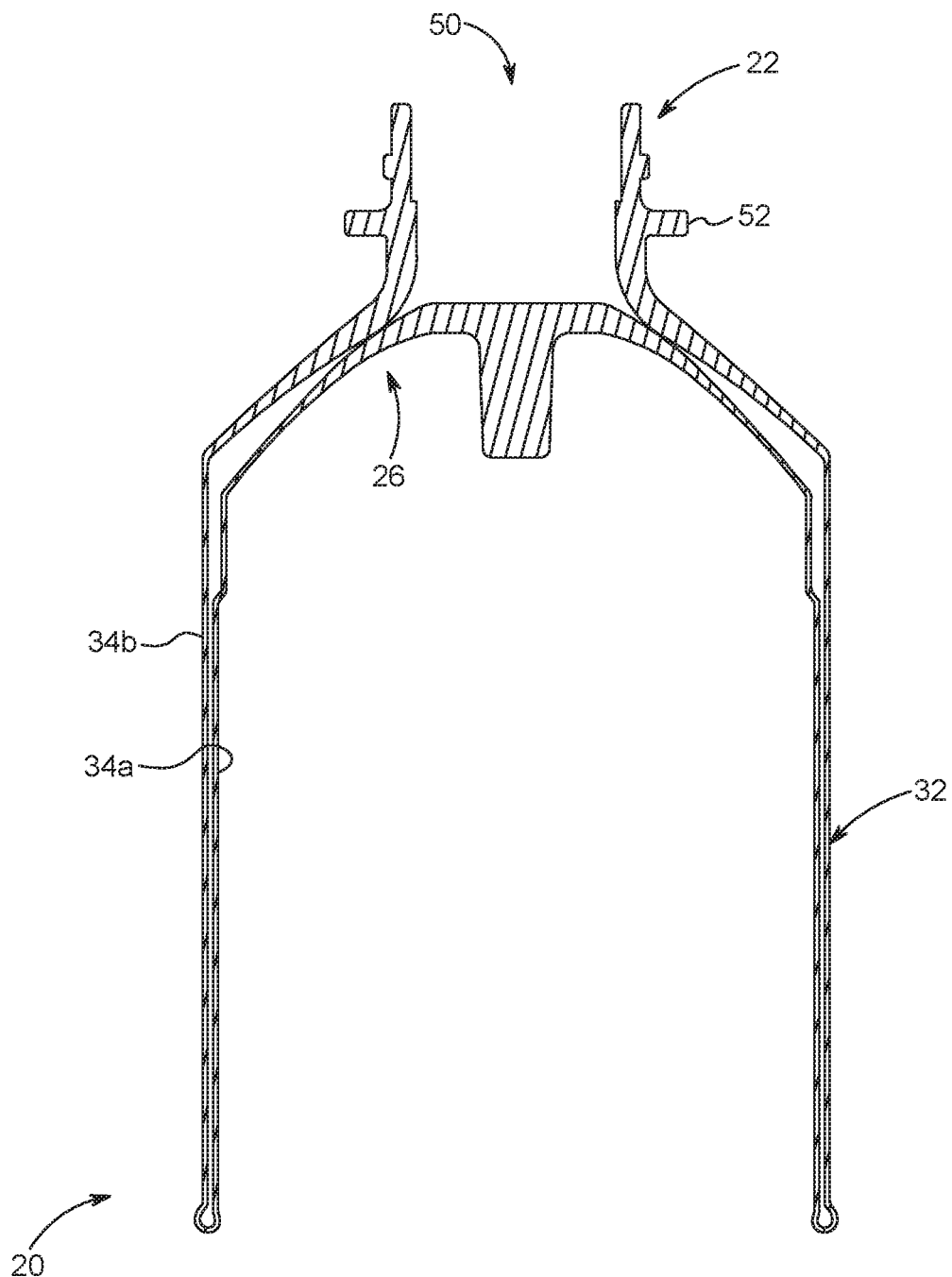

According to specific embodiments, the syringe may be PET or copolymer thereof, such as a medical grade polymer selected from EASTAR™ MN021 and EASTAR™ MN052, commercially available from Eastman Chemical Co. For various embodiments of the rolling diaphragm syringe 20, two portions of the inner surface 34a,b of the syringe 20 roll and slide over each other while in abutting contact as the syringe is rolled and unrolled, for example during an injection procedure. For example, as illustrated in FIGS. 3 and 5, in the unrolled and rolled configuration of the rolling diaphragm syringe 20, respectively, proximal inner surface 34a is rolled and slides over distal inner surface 34b during the rolling and unrolling process. A discussion of the physical process including rolling and unrolling of the syringe walls may be found, for example in International Application No. PCT/US2019/016621, the disclosure of which is incorporated by this reference.

In some examples, the rolling diaphragm syringe 20 may be reusable, meaning that the syringe 10 can be rolled and unrolled multiple times before being disposed of or recycled. For example, the rolling diaphragm syringe 20 can be filled as described above, rolled to deliver fluid contained therein to the patient, and then unrolled and re-filled several times to deliver additional doses of fluid to a patient. Alternatively, when utilized with a single-patient fluid path with appropriate check valves and connectors to prevent cross-contamination between patients, the rolling diaphragm syringe 20 may be used as a multi-patient syringe, with the single-patient portion of the fluid path being disposed of in between injection procedures. Alternatively, the rolling diaphragm syringe 20 may be a single-use component that is disposed of after each patient use.

Figure 6:
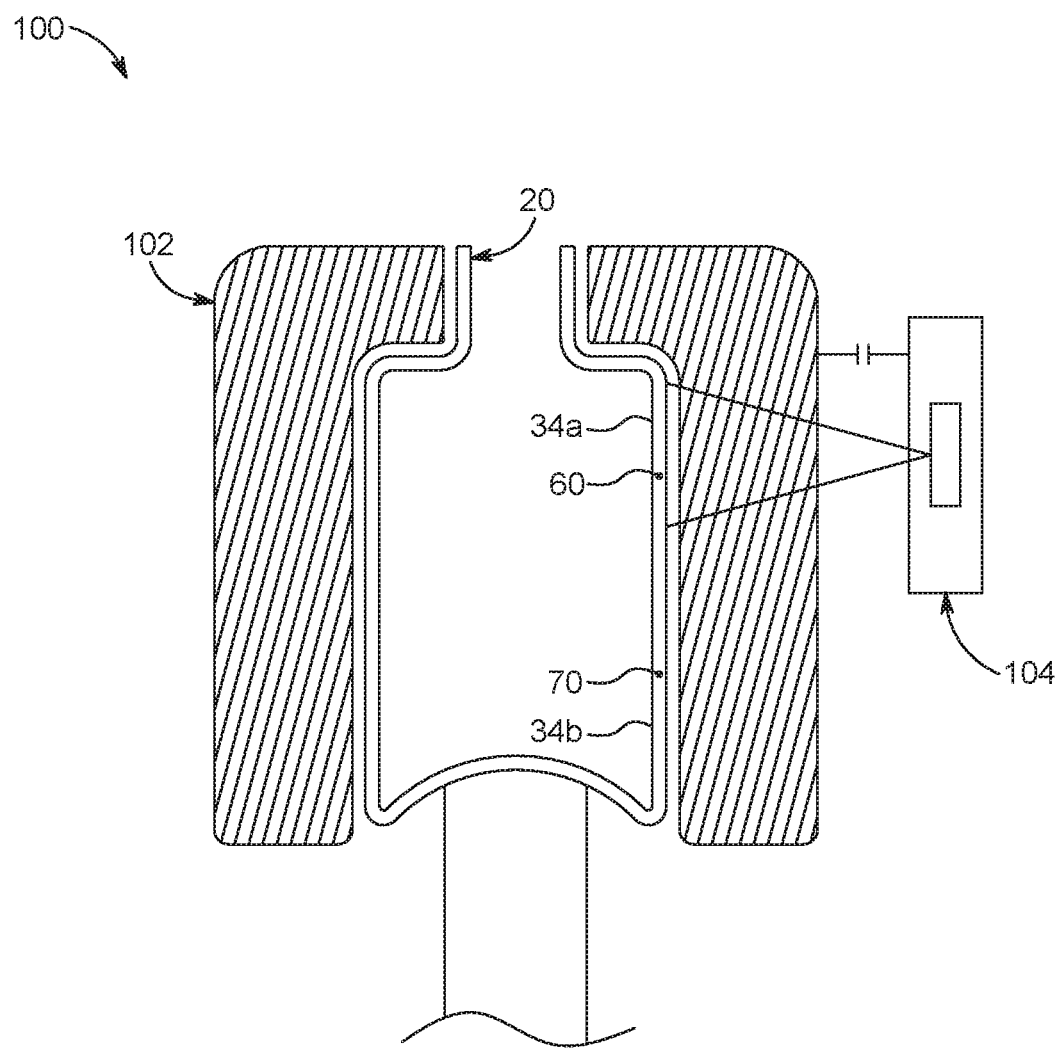
FIG. 6 is a schematic cross sectional view of a system for manufacturing the rolling diaphragm syringe of FIGS. 2 through 5.

According to various embodiments of the present disclosure, the amorphous or crystalline nature of the polymeric material of the rolling diaphragm syringe may be selectively controlled by a precise directed or targeted heating of one or more portions of the rolling diaphragm syringe or the preform of the syringe, prior to blow-molding, by a directed beam of energy, such as an beam of electromagnetic radiation, for example from a laser or maser, a beam of sound waves, for example ultrasound, or other directed energy beam. According to one embodiment, the directed beam of energy is a laser. In accordance with some examples or aspects of the present disclosure, various properties of the polymeric material at specific selected sites on the rolling diaphragm syringe 20 may be controlled or changed to result in enhanced performance, for example by making one or more portions or regions of the polymeric material more rigid (increased crystallinity relative to adjacent portions) or more flexible (increased amorphous character relative to adjacent portions). For example and without limitation, FIG. 6 shows one example embodiment of a system 100 that may be employed to manufacture the rolling diaphragm syringe 20 of FIGS. 2 to 5. As shown, the system 100 includes a mold 102 or other holder of the syringe 20 and at least one laser 104 positioned proximate (e.g., without limitation, coupled to) the mold 102. The at least one laser 104 may be any suitable laser used in the welding of polymers, e.g., without limitation, $CO_2$ lasers, Nd:YAG lasers, Diode lasers and fiber lasers or any combination of lasers, as required by the heating process. Although the at least one laser 104 is depicted as being positioned proximate the mold 102, the laser 104 can be retrofitted into separate machinery to process preforms and/or blown articles to achieve precise crystallinity zones approaching areas as small as 0.001 inch. In various embodiments, the precise crystallinity zones achievable by the laser-heating described herein may range from 0.001 inch to 1.000 inch; and may display similar percent crystallinity over the entire heated zone. For example, the at least one laser 104 may be incorporated into the preform heater zones before the preform is introduced into the blow-mold, for examples where the preforms is heated above glass transition temperatures before being introduced into the blow-mold. Alternatively, the at least one laser 104 may be incorporated into the injection-mold for laser heat treating the preform 20a after the injection molding process. In still another embodiment, the preform 20a may be laser heat treated after removal from the injection-mold but prior to insertion into the blow-mold. The at least one laser 104 may also be employed in a secondary process after blow-molding has occurred to tune localized areas of the rolling diaphragm syringe 20. In certain embodiments, the rolling diaphragm syringe 20 may be laser heated after the blow-molding process, either while the syringe 20 is still in the blow-mold or after the rolling diaphragm has been removed from the blow-mold, for example, during a rolling process, as described in International Application No. PCT/US2019/018404, or before or after the rolling process. It will be apparent to one of skill in the art that the laser heating process may be performed at any of the recited times and may further be performed at two or more of the recited times during the manufacturing process.

The at least one laser 104 is configured to heat localized portions of the rolling diaphragm syringe 20 in order to modify the crystallinity of the material of the preform 20a or the rolling diaphragm syringe 20 in the heated portion with high precision and with sharp transition zones between the more crystalline, laser-heated portion and the less crystalline, more amorphous portions. According to other embodiments of the laser-heating processes described herein, the laser-heating may be on selected non-circumferential portions of the syringe or preform (i.e., the heated portion may not encompass the entire circumference of the syringe or preform), which is not generally possible using conventional heat treatment processes that heat the portion of the syringe or preform around the entire circumference of the heated zone. For example, conventional methods to increase crystallinity of various portions of a polymeric material involve use of infrared heating of portions of the material resulting around the circumference of the molded article and are generally less precise resulting is crystalline portions that slowly transition to the more amorphous portions over a length of the heated portion (i.e., portions of the molded article near the transition are heated less and display lower crystallinity than heated portions of the article that are away from the transition zone).

According to various embodiments of the presently described rolling diaphragm syringes and preforms having increased crystallinity as a result of precise laser-heating, the laser-heated more crystalline portions of the preform and/or rolling diaphragm syringe may have a percent crystallinity ranging from 30% to 90%, and in certain embodiments from 30% to 60%. The percent crystallinity of the laser heated portion may result from one or more of the original percent crystallinity of the initial polymer, the initial temperature of the article, the length of time that the material is subjected to laser heating, the temperature above the glass transition temperature that the polymer is heated to, the intensity or energy of the laser, the wavelength of the laser light, the size of the portion of the article being heated, the thickness of the polymeric material being heated, and combinations of any thereof.

According to certain embodiments, the at least one laser 104 can be precisely aimed and focused and can generate patterns on specific portions of the preform 20a and/or the rolling diaphragm syringe 20. In various embodiments, the at least one laser 104 may be integrated into the injection-mold or blow-mold 102 in order to replace or augment infrared heater technology that exists in known apparatus to heat preforms. In other embodiments, the at least one laser 104 may be used to laser heat the preform or blow-molded syringe outside of the mold. Although only one laser 104 is depicted in FIG. 6, it will be appreciated that a suitable alternative system may have any number and/or type of lasers positioned in any number of different configurations in order to perform the function of increasing the crystallinity in targeted portions of the preform 20a or the rolling diaphragm syringe 20.

In the depicted example illustrated in FIG. 6, the crystallinity in a first portion 60 of the rolling diaphragm syringe 20 may be greater than crystallinity in a second portion 70 of the rolling diaphragm syringe 20 as a result of application of precise heating above the glass transition temperature by the laser 104 on the first portion 60 and not the second portion 70. In one example embodiment, the material of the rolling diaphragm syringe 20 in the first portion 60 may be more crystalized than the second portion 70 as a result of application of heat by the laser 104. Specifically, the laser 104 may be employed to heat the first portion 60 above its glass transition temperature, but below its melting temperature. The first portion 60 thus may present as translucent or white in color, hard, strong, and/or stiff, as compared to the second portion 70. Furthermore, by modifying the crystallinity of the material of the rolling diaphragm syringe 20 in the first portion 60 with the laser 104, the distal inner surface 34a may have different properties than the proximal inner surface 34b. For example, because crystalized PET may have a lower coefficient of friction than non-crystalized PET, the proximal inner surface 34b may more readily slide over the distal inner surface 34a during the rolling and unrolling process. As a result, the first portion 60 can advantageously be modified to be more conducive to rolling and unrolling of the rolling diaphragm syringe 20. Further, because the second portion 70 may be more amorphous than the first portion 60, the polymeric material of second portion 70 may more flexible and more readily roll during the rolling and unrolling process.

It will be appreciated that according to an embodiment of the method for controlling crystallinity in the rolling diaphragm syringe 20 may include providing the blow-mold 102 and at least one laser 104 positioned proximate to the mold 102; disposing a preform on at least a portion of the mold 102; heating and injecting gas into the preform 20a in order to cause the preform 20a to assume a profile of an inner surface of the mold 102, thereby forming the rolling diaphragm syringe 20; and heating at least one localized portion of a polymeric material of the preform 20a and/or the rolling diaphragm syringe 20 with the at least one laser 104 in order to form a crystalline region of material in the first portion 60 of the preform 20a or the rolling diaphragm syringe 20. The first localized crystalline region 60 of the polymeric material may have a crystallinity that is greater than a crystallinity in a portion 70 of the preform 20a or the rolling diaphragm syringe 20 that is not laser heated. In those embodiments where the polymeric material of the preform 20a is heated with the laser to increase the localized crystallinity, the laser heating step occurs prior to the blow-molding step of the method (i.e., before the preform 20a is heated and is pressurized with a gas to expand the polymeric material against the inner surface of mold 102.

According to another embodiment, the present disclosure provides the system 100 for heating at least one localized portion of a polymeric material of the preform 20a and/or the rolling diaphragm syringe 20 may include a fixture (e.g., the mold 102) having a profile shaped substantially the same as a profile of the rolling diaphragm syringe 20, and at least one laser 104 positioned proximate to the fixture and structured to form at least one crystalline region of material in the first portion 60 in the rolling diaphragm syringe 20. The localized crystalline region 60 of the polymeric material may have a crystallinity that is greater than a crystallinity in a portion 70 of the preform 20a or the rolling diaphragm syringe 20 that is not heated with the least one laser to a temperature above the glass transition temperature.

Figure 7:
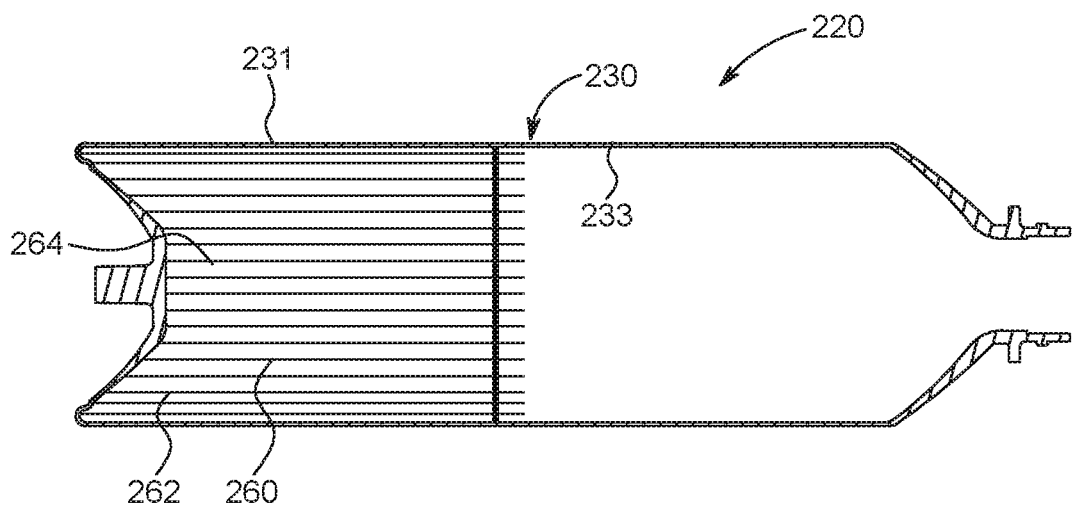
FIG. 7 is a cross sectional view of another rolling diaphragm syringe, shown in a completely unrolled configuration, in accordance with another non-limiting example of the present disclosure.
Figure 8:
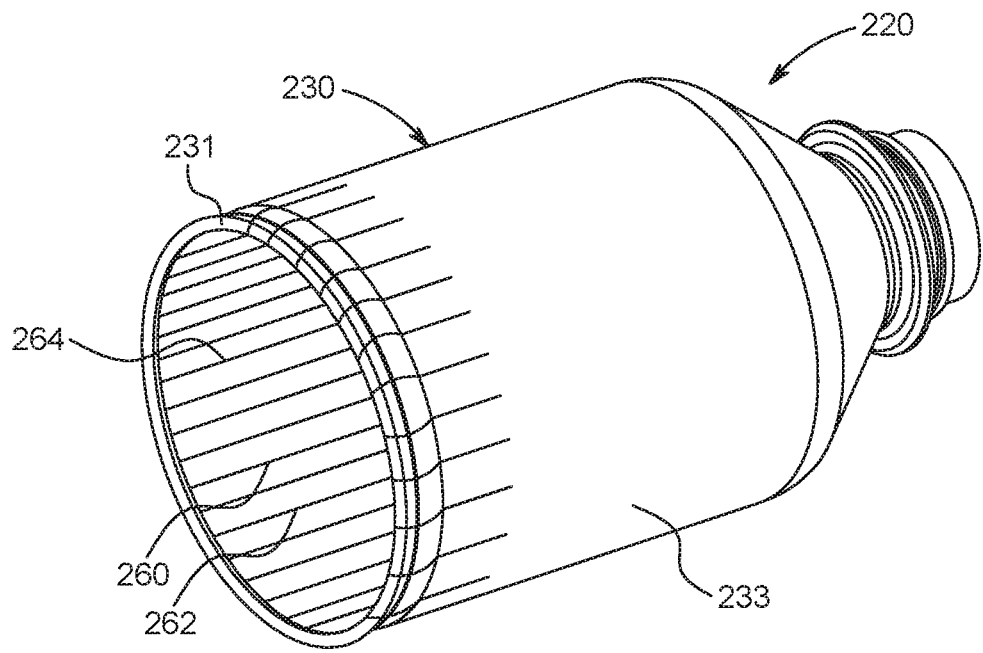
FIG. 8 is a perspective view of the rolling diaphragm syringe of FIG. 7, shown in a rolled configuration.

In other embodiments, although the at least one laser 104 may be focused on the first portion 60 in general, the at least one laser 104 may be employed in other more focused manners. For example, as described in International PCT Application PCT/US2019/016621, it is shown that texturization of the inner surfaces of the rolling diaphragm syringe 20 may impart desired properties, such as reduced friction during rolling and unrolling, and reduced audible noise as surfaces slide over one another. In certain embodiments, the methods for targeted increased crystallinity of specific portions of the rolling diaphragm syringe may allow for formation of texturized features on the interior surfaces of the rolling diaphragm syringe 20 without imparting these texturized features during a molding process. For example and without limitation, FIGS. 7 and 8 show different views of another rolling diaphragm syringe 220 manufactured by a similar process as the rolling diaphragm syringe 20, discussed herein. As shown, the sidewall 230 of the rolling diaphragm syringe 220 has a first half portion 231 and a second half portion 233. The first half portion 231 may have a plurality of crystalized portions 260, 262, 264 in the form of longitudinal ridges extending along the sidewall 230 parallel to the longitudinal axis. In accordance with some examples or aspects of the present disclosure, the crystalized portions 260, 262, 264 may be formed with at least one laser such as the at least one laser 104 illustrated in FIG. 6. The at least one laser 104 may form the crystalized portions 260, 262, 264 by heating the material (e.g., without limitation, PET) either in the preform or in the rolling diaphragm syringe in precise and selected regions above their glass transition temperatures but below their melting temperatures.

Figure 9:
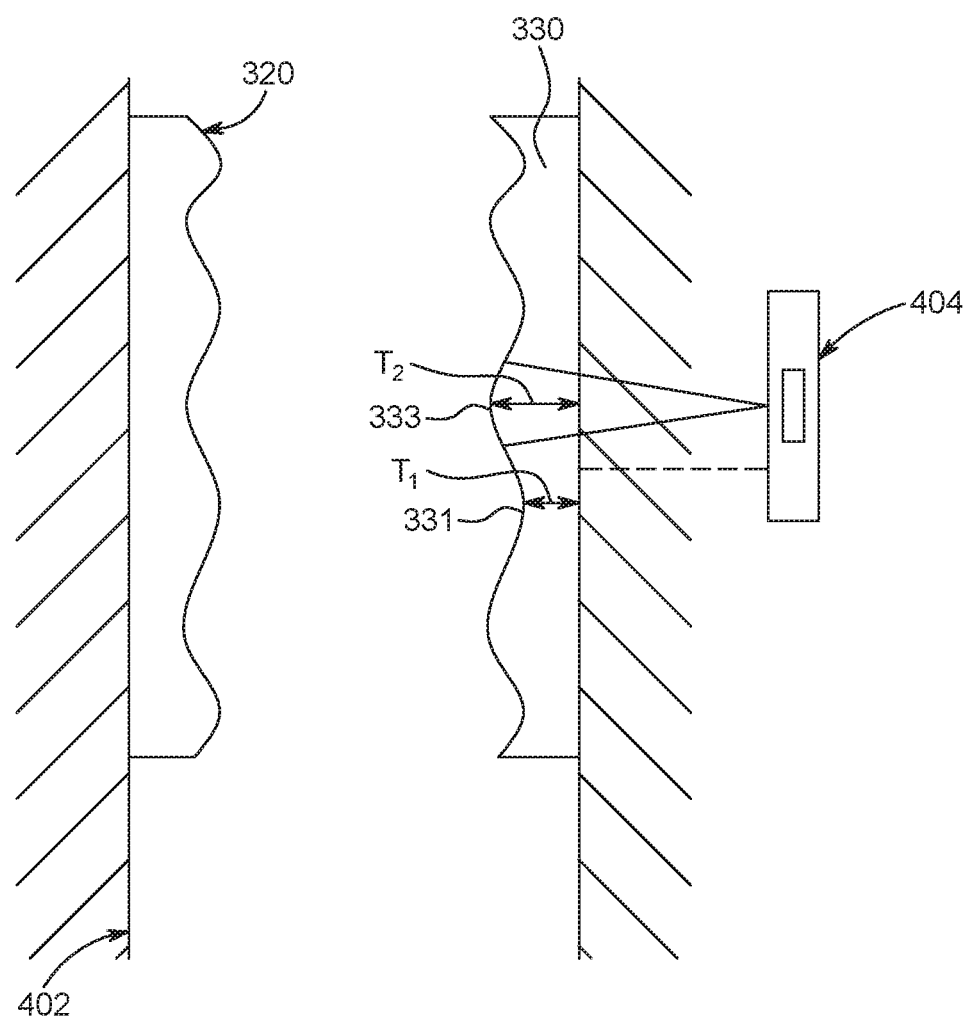
FIG. 9 is a schematic cross sectional view of another rolling diaphragm syringe, as employed in a fixture, in accordance with another non-limiting example of the present disclosure.

In certain embodiments, crystallized portions may be formed by laser heating the corresponding portions of the preform 20a, which are then transferred to the rolling diaphragm syringe 20 during the blow-molding process. According to this embodiment, the amorphous portions of the preform sidewall will stretch and expand during the blow-molding process whereas laser-heated, more crystalline portions of the preform will stretch and expand less, resulting in a syringe sidewall that is thicker at the more crystalline sections 333 than at the more amorphous sections 331. As illustrated in the close-up view in FIG. 9, as the blow-molding process expands the sidewall 330 against the side of the mold 402, the thicker crystalline sections 333 will be pressed radially inward to form ridges having greater thickness $T_2$ on the interior surface of the rolling diaphragm syringe 320 compared to the adjacent amorphous sections 331 having a thickness $T_1$ that is less than $T_2$, thereby providing a texturized inner surface of the resulting rolling diaphragm syringe 320. In accordance with certain embodiments, the at least one laser 404 may be positioned proximate or coupled to the mold fixture 402, and may be employed to control the thickness of the sidewall 330 to improve performance.

Alternatively, in another embodiment, the rolling diaphragm syringe 220 may be laser heated to form more crystalline regions 260, 262, 264 directly that may reduce friction as the proximal sidewall 231 slides over the distal sidewall 233.

The crystalized portions 260, 262, 264 may advantageously assist in reducing friction as the rolling diaphragm syringe 220 is rolled and unrolled. It will be appreciated that by manufacturing the crystalized portions 260, 262, 264 with the at least one laser 104, other, less cost-efficient methods of improving the rolling and unrolling operations, may be avoided. Additionally, although the more crystalline portions 260, 262, 264 are shown extending longitudinally along the first portion 231, other suitable alternative configurations that perform the desired function of reducing friction during the rolling and unrolling operations are contemplated herein. For example, the more crystalline portions 260, 262, 264 may be helical, dotted, or cross-hatched patterns, as described in International PCT Application PCT/US2019/016621, that cannot be readily applied using conventional molding techniques.

Figure 10:
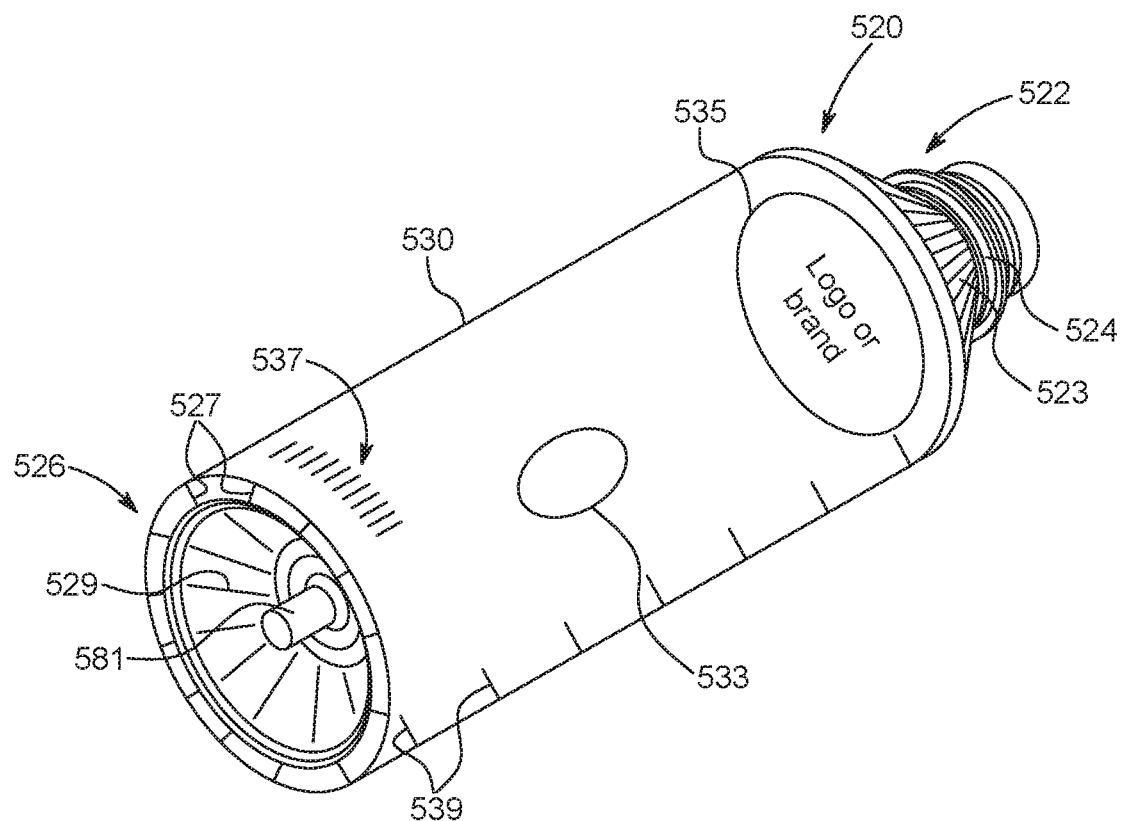
FIG. 10 is a perspective view of another rolling diaphragm syringe, in accordance with another non-limiting example of the present disclosure.

FIG. 10 shows a perspective view of another embodiment of a rolling diaphragm syringe 520, in accordance with the present disclosure. According to various embodiments, the at least one laser 104, 404 may be employed to impart other beneficial features to the rolling diaphragm syringe 520. For example and without limitation, the sidewall 530 of the rolling diaphragm syringe 520 may have a fluid fill indicator 533 formed in a portion thereof as described in U.S. Pat. No. 5,254,101, the disclosure of which is incorporated herein, and the fluid fill indicator 533 may have its crystallinity changed by a laser, such as the at least one laser 104, 404 so that it is opaque compared to the adjacent material. The fluid fill indicator 533 may have a defined shape, such as an oval shape that widens, for example to a circle, when viewed through a liquid fluid (such as a contrast agent or saline) contained the rolling diaphragm syringe 20 is filled, as compared to when having no substantial change in the defined shape when viewed through the rolling diaphragm syringe 20 with it is filled with air. The fluid fill indicator 533 may be employed to provide visual identification whether the rolling diaphragm syringe is filled with air or filled with a fluid. In another embodiment, the indicia may be in the form of a usage indicator to indicate whether a syringe has been previously used. According to this embodiment, a first high-crystallinity mark may be formed on an inside, outside, or interior of a first region of the syringe sidewall which is aligned with a second high-crystallinity mark on an inside, outside, or interior of a second region of the syringe sidewall when the syringe is in the initial rolled configuration. After the syringe has been used (i.e., unrolled during a filling process and re-rolled during a delivery process), the first and second marks will not be aligned as in the original rolled configuration, indicating that the syringe has been used and, if necessary, should be disposed of for safety reasons. The alignment or misalignment of the first and second marks may be visualized by the user or by the system, such as using an image recognition system, such as described in PCT Publication No. WO 2017/040152, the disclosure of which is incorporated herein by this reference.

In certain embodiments, the distal end 522 may have a fill verification region 823 (see, e.g., FIG. 13), as described in U.S. Application Publication No. 2017/0056603 and U.S. Pat. No. 10,201,666, the disclosures of which are incorporated herein by reference, formed or highlighted by crystalized areas created with the at least one laser 104, 404. In still other embodiments, the discharge neck 524 and/or other portions of the distal end 522 may have crystalized zones, created with the at least one lasers 104, 404, in the finish areas to enhance any laser welding of syringe caps, e.g., by allowing easier laser absorption or providing greater strength at the distal conical end 522 to better withstand pressures within the syringe during an injection procedure.

In other embodiments, the sidewall 530, or a suitable alternative region of the rolling diaphragm syringe 520, may be provided with a logo or brand 535, or other suitable marking, said marking being provided with the at least one laser 104, 404, for example by laser heating the polymeric material with a laser in increase the crystallinity and opacity of the specific regions to form letters, numbers, and/or images on the sidewall 530.

In other embodiments, the sidewall 530, or a suitable alternative region of the rolling diaphragm syringe 520, may be provided with a barcode or other visual marking indicia 537, the barcode 537 being provided with the at least one laser 104, 404, by laser heating the polymeric material with a laser in increase the crystallinity and opacity of the specific regions. The barcode 537 may be provided on a preform, e.g., for example by laser heating and increasing the crystallinity and opacity of the relatively thick area of polymeric material of the preform, which may then be blow-molded into the rolling diaphragm syringe 520, or, alternatively, it may be provided on the rolling diaphragm syringe 520 after it has been blown into shape. Additionally, although the barcode 537 is depicted in FIG. 10 as being a one-dimensional barcode 537, suitable alternative barcodes, e.g., two-dimensional barcodes (not shown), such as QR codes, made in a similar manner by increasing the crystallinity and opacity of the polymeric material as the barcode 537, are contemplated herein.

According to other embodiments, the sidewall 530 may be provided with fluid level graduations (two graduations 539 are indicated) extending along at least a portion of a length thereof. These graduations may be provided with the at least one laser 104, 404 by increasing the crystallinity and opacity of the polymeric material.

Still referring to FIG. 10, in certain embodiments the flare area of the proximal end 526 of rolling diaphragm syringe 520 may be laser heated in precise regions or sections (two of the regions 527 are indicated in FIG. 10) with the at least one laser 104, 404 beyond their glass transition temperatures but below their melting points and, when accurately controlled, the regions 527 could advantageously reduce the required roll force, thereby improving rolling performance.

In another embodiment, the concave shaped area of the proximal end 526, e.g., the end wall, could also be provided with more crystalline portions 529 by the at least one laser 104, 404, in order to perform the desired function of increasing the inversion strength in this area. Accordingly, the rolling diaphragm syringe 520 may be able to withstand inversion of the proximal end 526 during fill better than known rolling diaphragm syringes.

It will be appreciated that any combinations of any of the features described herein and in FIG. 10 may be incorporated into rolling diaphragm syringe 520 and providing these features with the at least one laser 104, 404 may significantly simplify and improve manufacturing of the described rolling diaphragm syringes 520. Additionally, suitable alternative rolling diaphragm syringes may have any number and/or configuration of the aforementioned features of the rolling diaphragm syringe 520, without departing from the scope of the present disclosure.

Figure 11:
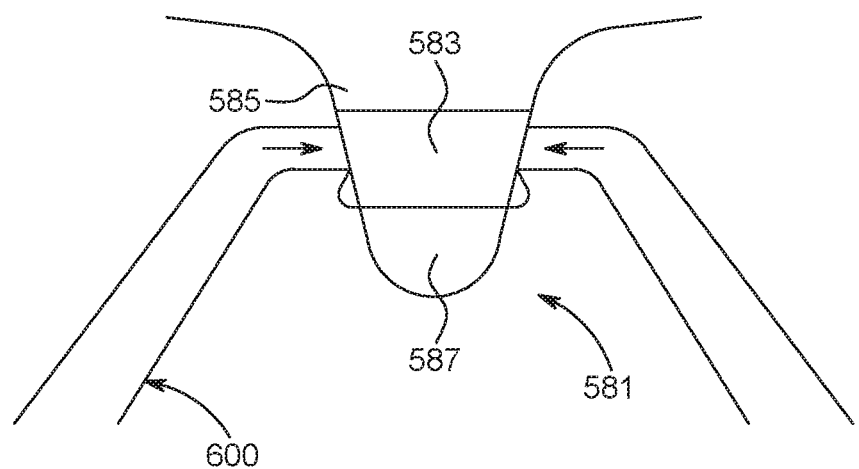
FIG. 11 is an enlarged view of a portion of the rolling diaphragm syringe of FIG. 10, shown as employed with a tool.

Continuing to refer to FIG. 10, and to FIG. 11, the proximal end 526 of the rolling diaphragm syringe 520 may have a piston engagement portion 581. The piston engagement portion 581 may provide a structure for engagement elements 600 on a piston of the fluid injector to grab onto to assist with unrolling and filling of the rolling diaphragm syringe 520, such as during filling of the rolling diaphragm syringe 520 with fluid. As shown in FIG. 11, according to certain embodiments a first portion 583 of the piston engagement portion 581 may be formed from a material that is more amorphous than the material of surrounding second and third portions 585, 587. The more amorphous nature of first portion 583 may allow for the engagement elements 600 to engaged and dig into the softer, amorphous polymer of portion 583, thereby increasing the gripping or attachment force of the engagement element 600 with the piston engagement portion 581. According to one embodiment, the second and/or third portions 585, 587 may be laser heated to increase the crystallinity and strength of the polymeric material. In particular, increasing the crystallinity and strength of third portion 587 may provide a retention ledge for the engagement elements 600 to prevent the engagement elements from slipping of the proximal end of the piston engagement portion 581.

In another embodiment of the piston engagement portion 581, the first portion 583 may be formed in this manner by heating the material with the at least one laser 104, 404 beyond its melting temperature to make the first portion 583 more amorphous in order to allow the engagement element 600 to more easily grasp and dig into the first portion 583 during use compared to the second and/or third portions 585, 587.

Figure 12:
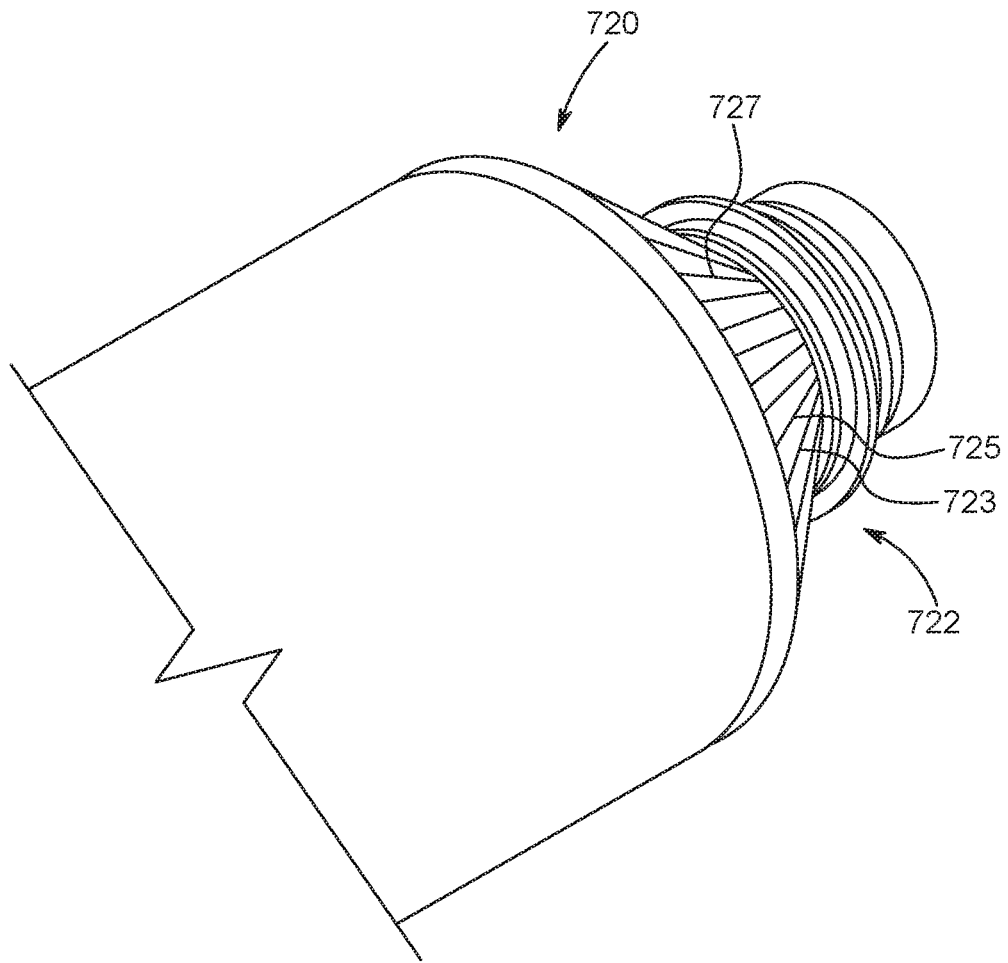
FIG. 12 is a perspective view of a portion of another rolling diaphragm syringe, in accordance with another non-limiting example of the present disclosure.

FIG. 12 shows a perspective view of a portion of another rolling diaphragm syringe 720, in accordance with another non-limiting embodiment of the present disclosure. As shown, the distal end 722 of the rolling diaphragm syringe 720 is provided with a number of laser heat treated precise crystalline portions 723, 725, 727 on a frusto-conical shaped portion thereof. The precise crystalline portions 723, 725, 727 may be formed in substantially the same manner as the precise crystalline portions 260, 262, 264, discussed herein, and may display increased strength compared to the more amorphous, non-laser heated portions. Accordingly, because the distal end 722 may be associated with relatively high stresses, e.g., during rolling wherein fluid pressures build up proximate the distal end 722, having the crystalline portions 723, 725, 727 provides increased strength to the distal end 722. It will also be appreciated that the crystalized portions 723, 725, 727 allow for relatively low syringe capacitance (i.e., swelling of the walls of the syringe under the fluid pressures during injection procedures) by preventing expansion of the frusto-conical shaped distal end 722. Additionally, while the crystalized portions 723, 725, 727 are provided as being on the frusto-conical shaped portion of the distal end 722, it will be appreciated that more crystalline portions may be provided on any location of the distal end 722 in order to achieve the desired function of helping the rolling diaphragm syringe 720 to withstand the relatively high fluid pressures associated with use. This further provides an improved mechanism to handle high injection pressures with less capacitance.

Figure 13:
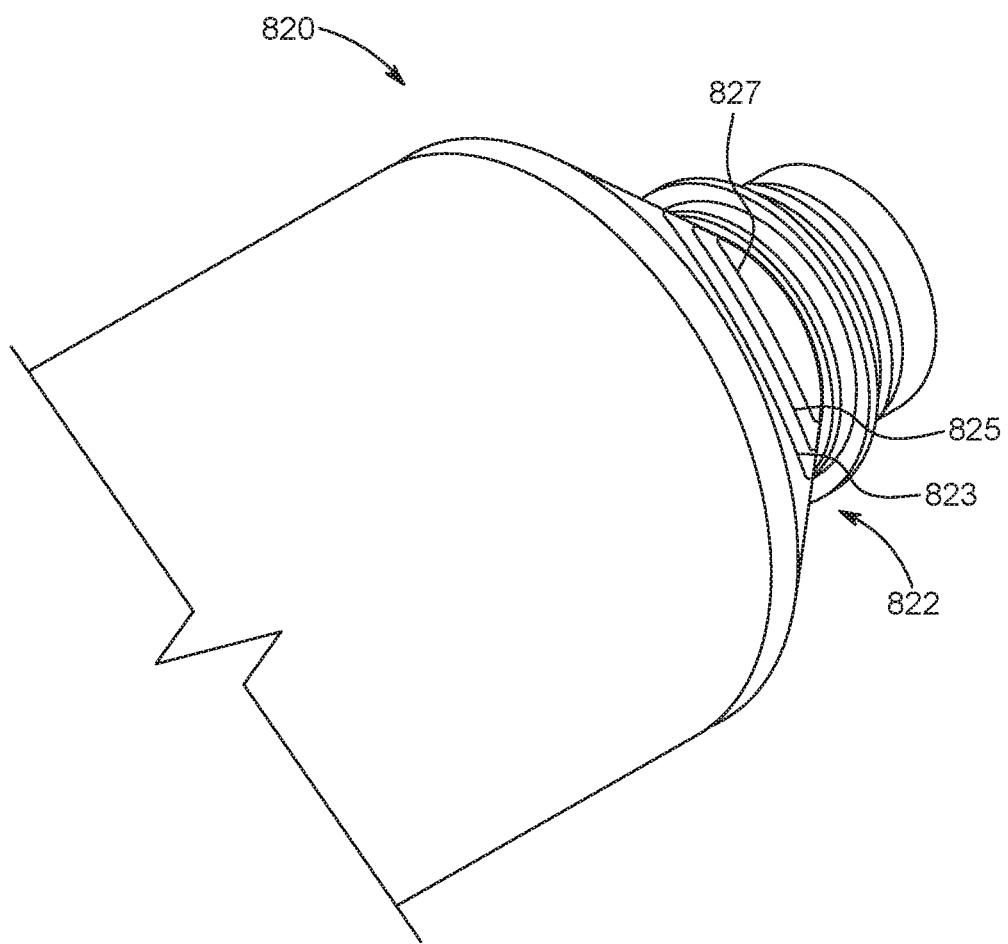
FIG. 13 is a perspective view of a portion of another rolling diaphragm syringe, in accordance with another non-limiting example of the present disclosure.

FIG. 13 shows a perspective view of a portion of another embodiment of a rolling diaphragm syringe 820 of the present disclosure. As shown, the distal end 822 of the rolling diaphragm syringe 820 has a number of crystalline portions 823, 825, 827, each functioning in substantially the same manner as the crystalline portions 723, 725, 727, discussed herein. However, as shown, the crystalline portions 823, 825, 827 are annular-shaped. Other orientations and patters of the crystalline portions are contemplated to increase the strength of the distal frusto-conical end 722 and are within the scope of the present disclosure.

As discussed above, employing the at least one laser 104, 404 allows for localized semi non-stretch zones to be provided in preforms and rolling diaphragm syringes (e.g., the rolling diaphragm syringes 20, 220, 320, 520, 720) that enables shapes and features in syringes that are not currently possible. Additionally, it is known that syringes are often exposed to relatively high temperatures (e.g., greater than about 60° C.) during shipping, a factor that undesirably contributes to volumetric shrinkage of known syringes. By employing the at least one laser 104, 404 to create features (e.g., the crystalized portions 260, 262, 264, 723, 725, 727 and/or other regions 523, 527), volumetric shrinkage may be reduced. Furthermore, it is to be understood that oxygen barrier properties may also be enhanced by adding crystalline zones in that heating and stretching of PET forms the presence of impermeable gas crystal structures in the PET matrix.

Furthermore, in accordance with the disclosed concept, the at least one laser 104, 404 may be employed to create deliberate localized amorphous portions or zones in the syringes. That is, the at least one laser 104, 404 may be employed to heat specific portions of the polymeric material beyond their glass transition temperatures where they would crystalize, and continue to heat them greater than their melting temperatures where the polymeric structure becomes more amorphous, thereby providing for advantageous features such as localized flexibility in these portions.

Finally, although the disclosed concept has been described in association with the at least one laser 104 positioned proximate the mold 102, it will be appreciated that suitable alternative lasers may be employed separate from the mold 102, such as for example, to form crystalized portions in a preform before the preform is introduced into the mold 102, or in a fixture after the rolling diaphragm syringe has been removed from the mold 102. Accordingly, a preform, e.g., preform 20a in FIG. 1B, may have a proximal end having an end wall, a distal end having an open-ended discharge neck, and a sidewall extending between the proximal end and the distal end along a longitudinal axis, with crystallinity of a material of the preform 20a in a first portion of the preform 20a is different than crystallinity in a second portion of the preform 20a.

While examples of a fluid delivery system and a syringe for use therefor were provided in the foregoing description, those skilled in the art may make modifications and alterations to these examples without departing from the scope and spirit of the disclosure. Accordingly, the foregoing description is intended to be illustrative rather than restrictive. The disclosure described hereinabove is defined by the appended claims, and all changes to the disclosure that fall within the meaning and the range of equivalency of the claims are to be embraced within their scope.

We claim:

1. A fluid container comprising:
    a proximal end having an end wall;
    a distal end having an open-ended neck; and
    a sidewall extending between the proximal end and the distal end along a longitudinal axis,
    wherein the fluid container includes at least a first crystalline region having a size ranging from 0.001 inch to 1.000 inch and at least a second region,
    wherein a precise localized crystallinity of a polymeric material of the fluid container of the first crystalline region of the fluid container is greater than a crystallinity of the polymeric material of the fluid container of at least the second region,
    wherein the precise localized crystallinity of the first crystalline region has a percent crystallinity ranging from 30% to 90% and is formed by heating the polymeric material of the first crystalline region to a temperature above a glass transition temperature of the polymeric material but below a melting temperature of the polymeric material with a beam of electromagnetic radiation in a form of a laser such that a transition zone between the first crystalline region and the second region is sharper than a transition zone between a first infrared heated crystalline region and a second region that is not infrared heated.

2. The fluid container of claim 1, wherein the polymeric material is selected from the group consisting of polyethylene terephthalate, polyethylene terephthalate glycol, polyethylene, polypropylene, polystyrene, polyvinyl chloride, polybutadiene, polyethylene oxide, poly(p-phenylene terephthalamide), polytetrafluoroethylene, polyoxymethylene, polybutylene terephthalate, polypropylene random copolymer, polypropylene impact copolymer, polypropylene homopolymer, acrylonitrile butadiene styrene, cyclic olefin polymer, cyclic olefin copolymer, multilayer polypropylene, polycarbonate, ethylene vinyl acetate, nylon 6, nylon 8, nylon 12, nylon 6,6, nylon 6,10, and co-polymers or mixtures or layers of any thereof.

3. The fluid container of claim 1, wherein the polymeric material is polyethylene terephthalate.

4. The fluid container of claim 1, wherein the polymeric material is a multi-layer material comprising at least one layer of polymeric material selected from the group consisting of polyethylene terephthalate, polyethylene terephthalate glycol, polyethylene, polypropylene, polystyrene, polyvinyl chloride, polybutadiene, polyethylene oxide, poly (p-phenylene terephthalamide), polytetrafluoroethylene, polyoxymethylene, polybutylene terephthalate, polypropylene random copolymer, polypropylene impact copolymer, polypropylene homopolymer, acrylonitrile butadiene styrene, cyclic olefin polymer, cyclic olefin copolymer, multilayer polypropylene, polycarbonate, ethylene vinyl acetate, nylon 6, nylon 8, nylon 12, nylon 6,6, nylon 6,10, and co-polymers or mixtures of any thereof.

5. The fluid container of claim 1, wherein at least a portion of at least the first crystalline region is on the end wall of the fluid container.

6. The fluid container of claim 1, wherein at least a portion of at least the first crystalline region is on the sidewall of the fluid container.

7. The fluid container of claim 1, wherein at least a portion of at least the first crystalline region is on the distal end of the fluid container.

8. The fluid container of claim 1, wherein the fluid container is a syringe and the end wall comprises a proximal surface of a plunger.

9. The fluid container of claim 1, wherein the fluid container is a rolling diaphragm syringe,
    wherein at least a portion of the sidewall is flexible such that the sidewall rolls upon itself with an outer surface of the sidewall at a folding region being folded in a radially inward direction when acted upon by an external force in a direction from the proximal end toward the distal end, and wherein the sidewall unrolls with the outer surface of the sidewall at the folding region being unfolded in a radially outward direction when acted upon by the external force in a direction from the distal end toward the proximal end.

10. The fluid container of claim 1, wherein the precise localized crystallinity of at least the first crystalline region is in the form of one or more of letters, numbers, images, barcodes, and other indicia at the first crystalline region of the fluid container.

11. The fluid container of claim 1, wherein the precise localized crystallinity of the fluid container changes at least one material property of the polymeric material of at least the first crystalline region.

12. The fluid container of claim 11, wherein the at least one material property is selected from the group consisting of opacity, rigidity, flexibility, brittleness, softness, strength, coefficient of friction, stretch, gas permeability, and combinations of any thereof.

13. The fluid container of claim 1, wherein the fluid container is a beverage container.

14. A method for locally controlling crystallinity of a polymeric material in a fluid container, the method comprising:
- injection molding a preform for the fluid container within an injection-mold;
- placing the preform into a blow-mold for blow-molding the fluid container;
- heating and injecting gas into the preform to cause the preform to expand against an inner surface of the blow-mold, thereby forming the fluid container; and
- laser heating at least one precise localized portion of the polymeric material of the preform or the fluid container with at least one laser to above a glass transition temperature of the polymeric material but below a melting temperature of the polymeric material to form a first precise localized crystalline region of the polymeric material, wherein the first precise localized crystalline region has a percent crystallinity ranging from 30% to 90%,
- wherein the first precise localized crystalline region of the polymeric material has a size ranging from 0.001 inch to 1.000 inch and has a crystallinity that is greater than a crystallinity in a second region of the preform or the fluid container that is not laser heated, and a transition zone between the first precise localized crystalline region and the second region is sharper than a transition zone between a first infrared heated crystalline region and a second crystalline region that is not infrared heated.

15. The method of claim 14, wherein the fluid container is a syringe.

16. The method of clam 14, wherein the fluid container is a rolling diaphragm syringe,
wherein at least a portion of a sidewall of the rolling diaphragm syringe is flexible such that the sidewall rolls upon itself with an outer surface of the sidewall at a folding region being folded in a radially inward direction when acted upon by an external force in a direction from a proximal end toward a distal end of the rolling diaphragm syringe, and wherein the sidewall of the rolling diaphragm syringe unrolls with the outer surface of the sidewall at the folding region being unfolded in a radially outward direction when acted upon by the external force in a direction from the distal end toward the proximal end of the rolling diaphragm syringe.

17. The method of claim 14, wherein the crystallinity of at least the first precise localized crystalline region is in a form of one or more of letters, numbers, images, barcodes, and other indicia at the first precise localized crystalline region of the fluid container.

18. The method of claim 14, wherein the polymeric material comprises polyethylene terephthalate.

19. The method of claim 14, wherein the polymeric material comprises a multi-layered polymeric material and wherein laser heating at least one localized portion of the polymeric material further comprises:
- laser heating one or more layers of the multi-layer polymeric material with the at least one laser according to a laser depth focus, a laser light wavelength, and combinations thereof.

20. The method of claim 14, wherein the fluid container is a beverage container.

21. A preform for blow-molding a fluid container, the preform comprising:
- a proximal end;
- a distal end having an open-ended neck; and
- a sidewall extending between the proximal end and the distal end along a longitudinal axis,
- wherein a polymeric material of at least a first localized laser-heated crystalline region of the preform has a percent crystallinity ranging from 30% to 90% crystallinity, and wherein a percent crystallinity of an amorphous polymeric material of an adjacent second region of the preform is less than 10% crystallinity.

* * * * *

UNITED STATES PATENT AND TRADEMARK OFFICE
CERTIFICATE OF CORRECTION

PATENT NO. : 12,077,338 B2
APPLICATION NO. : 17/625814
DATED : September 3, 2024
INVENTOR(S) : Spohn et al.

Page 1 of 1

It is certified that error appears in the above-identified patent and that said Letters Patent is hereby corrected as shown below:

In the Specification

In Column 3, Line 53, delete "least" and insert -- at least --, therefor.
In Column 4, Line 48, delete "terephthalate" and insert -- terephthalate, --, therefor.
In Column 6, Line 34, delete "least" and insert -- at least --, therefor.
In Column 7, Line 57, delete "no" and insert -- not --, therefor.
In Column 7, Line 67, delete "etc.)," and insert -- etc., --, therefor.
In Column 8, Line 36, delete "18a" and insert -- 180° --, therefor.
In Column 8, Line 41, delete "of at" and insert -- of --, therefor.
In Column 9, Line 47, delete "etc.)," and insert -- etc., --, therefor.
In Column 10, Line 11, delete "bottle)" and insert -- bottle). --, therefor.
In Column 11, Line 44, delete "rely of" and insert -- rely on --, therefor.
In Column 12, Line 41, delete "resin" and insert -- resin is --, therefor.
In Column 12, Line 57, delete "herein" and insert -- herein as --, therefor.
In Column 16, Line 65, delete "proximate" and insert -- proximate to --, therefor.
In Column 17, Line 49, delete "is" and insert -- in --, therefor.
In Column 18, Line 46, delete "may" and insert -- may be --, therefor.
In Column 19, Line 2, delete "mold 102." and insert -- mold 102). --, therefor.
In Column 19, Line 17, delete "least" and insert -- at least --, therefor.
In Column 20, Line 44, delete "contained" and insert -- contained in --, therefor.
In Column 22, Line 20, delete "engaged" and insert -- engage --, therefor.
In Column 22, Line 29, delete "slipping of" and insert -- slipping off --, therefor.
In Column 22, Line 52, delete "proximate" and insert -- proximate to --, therefor.
In Column 23, Line 9, delete "patters" and insert -- patterns --, therefor.
In Column 23, Line 41, delete "proximate" and insert -- proximate to --, therefor.

In the Claims

In Column 26, Line 6, in Claim 16, delete "clam" and insert -- claim --, therefor.

Signed and Sealed this
Fourth Day of February, 2025

Coke Morgan Stewart
*Acting Director of the United States Patent and Trademark Office*